US008207116B2

(12) United States Patent
Franz et al.

(10) Patent No.: US 8,207,116 B2
(45) Date of Patent: Jun. 26, 2012

(54) REMEDIES FOR ISCHEMIA

(75) Inventors: Wolfgang M. Franz, Wessling (DE);
Hans Theiss, Munich (DE);
Marc-Michael Zaruba, Donzdorf (DE);
Stefan Brunner, Munich (DE)

(73) Assignee: Ludwig-Maximilians-Universitat Munchen, Munich (DE)

( * ) Notice: Subject to any disclaimer, the term of this patent is extended or adjusted under 35 U.S.C. 154(b) by 107 days.

(21) Appl. No.: 12/296,584

(22) PCT Filed: Apr. 12, 2007

(86) PCT No.: PCT/EP2007/003272
§ 371 (c)(1),
(2), (4) Date: Dec. 2, 2008

(87) PCT Pub. No.: WO2007/118680
PCT Pub. Date: Oct. 25, 2007

(65) Prior Publication Data
US 2009/0286730 A1 Nov. 19, 2009

(51) Int. Cl.
A61K 38/16 (2006.01)
A61K 38/19 (2006.01)
A61K 38/29 (2006.01)
(52) U.S. Cl. .................................. 514/11.8; 514/7.9
(58) Field of Classification Search .................. None
See application file for complete search history.

(56) References Cited

U.S. PATENT DOCUMENTS

| | | | |
|---|---|---|---|
| 7,393,827 B2 | 7/2008 | Nadler | |
| 7,579,189 B2 * | 8/2009 | Freyman et al. | 435/395 |
| 2003/0181373 A1 * | 9/2003 | Ohhashi | 514/12 |
| 2007/0021336 A1 | 1/2007 | Anderson et al. | |

FOREIGN PATENT DOCUMENTS

WO WO 2004/056186 A 7/2004
WO WO 2005/049062 6/2005

OTHER PUBLICATIONS

Ballen, et al., "Parathyroid hormone may improve autologous stem cell mobilization via the stem cell niche," 47th Annual Meeting of the American-Society-of-Hematology, 2005, p. 557A, vol. 106, No. 11, Part 1, Database accession No. PREV200600184338 abstract, XP002460695.
Calvi, et al., "Osteoblastic cells regulate the haematopoietic stem cell niche," Nature, 2003, pp. 841-846, vol. 425, No. 6960, Nature Publishing Group, London, GB, XP002389181.
Engelmann M.G., et al., "Stem cell therapy after myocardial infarction: ready for clinical application?," Current Opinion in Molecular Therapeutics, Current Drugs, 2006, pp. 396-414, vol. 8, No. 5, London, GB, XP008086268.
Engelmann, et al., "Autologous bone marrow stem cell mobilization induced by granulocyte colony-stimulating factor after subacute ST-segment elevation myocardial infarction undergoing late revascularization: final results from the G-CSF-STEMI (Granulocyte Colony-Stimulating Factor ST-Segment Elevation Myocardial Infarc," Journal of the American College of Cardiology, 2006, pp. 1712-1721, vol. 48, No. 8, USA, XP002460693.
Horowitz, et al., "Parathyroid hormone and lipopolysaccharide induce murine osteoblast-like cells to secrete a cytokine indistinguishable from granulocyte-macrophage colony-stimulating factor," Journal of Clinical Investigation, 1989, pp. 149-157, vol. 83, No. 1, USA, XP002460691.
Jansen J., et al., "Parathyroid hormone-related peptide improves contractile function of stunned myocardium in rats and pigs," American Journal of Physiology—Heart and Circulatory Physiology, vol. 284, No. 1, 2003, pp. H49-H55, USA, XP002460692.
Kocher, et al., "Neovascularization of ischemic myocardium by human bone-marrow-derived angioblasts prevents cardiomyocyte apoptosis, reduces remodeling and improves cardiac function," Nature Medicine, 2001, pp. 430-436, vol. 7, No. 4, USA, XP002963458.
Kuethe, et al., "Mobilization of stem cells by granulocyte colony-stimulating factor for the regeneration of myocardial tissue after myocardial infarction/Mobilisation von Stammzellen durch den Granuloyten-Kolonie stimulierenden Faktor zur Regeneration myyokardialen Gewebs nach Herzinfarkt/," Deutsche Medizinische Wochenschrift, 2004, pp. 424-428, vol. 129, No. 9, DE, XP008086248.
Orlic, et al., "Mobilized bone marrow cells repair the infarcted heart, improving function and survival," Proceedings of the National Academy of Sciences of USA, National Academy of Science, 2001, pp. 10344-10349, vol. 98, No. 18, USA, XP002216659.
Yin, et al., "The stem cell niches in bone," Journal of Clinical Investigation, 2006, pp. 1195-1201, vol. 116, No. 5, XP002460694.
Patrik Andersson et al.; "Primary hyperparathyroidism and heart disease—a review"; European Heart Journal (2004) 25, pp. 1776-1787. Jean-Pierre Lévesque et al.; "Disruption of the CXCR4/CXCL12 chemotactic interaction during hematopoietic stem cell mobilization induced by GCSF or cyclophosphamide"; The Journal of Clinical Investigation; Jan. 2003; vol. 111; No. 2; pp. 187-196.

* cited by examiner

Primary Examiner — Marianne P Allen
(74) Attorney, Agent, or Firm — Foley & Lardner LLP

(57) ABSTRACT

The present invention relates to uses and methods of parathyroid hormone (PTH), preferably PTH (1-34), and/or parathyroid hormone-related peptide (PTHrP), preferably PTHrP (1-34), for recruiting stem cells into tissue suffering from ischemia, wherein said stem cells are preferably capable of repairing and/or regenerating said tissue suffering from ischemia. Accordingly, the uses and methods of the present invention are preferably suitable for the prevention and/or treatment of ischemia. Moreover, the present invention relates to a composition comprising parathyroid hormone (PTH), preferably PTH (1-34), and/or parathyroid hormone-related peptide (PTHrP), preferably PTHrP (1-34), and/or G-CSF or a G-CSF fragment for use as a pharmaceutical composition. In a particular aspect, a DPP IV antagonist is applied in the uses, methods and/or compositions of the present invention.

12 Claims, 21 Drawing Sheets

Figure 4:
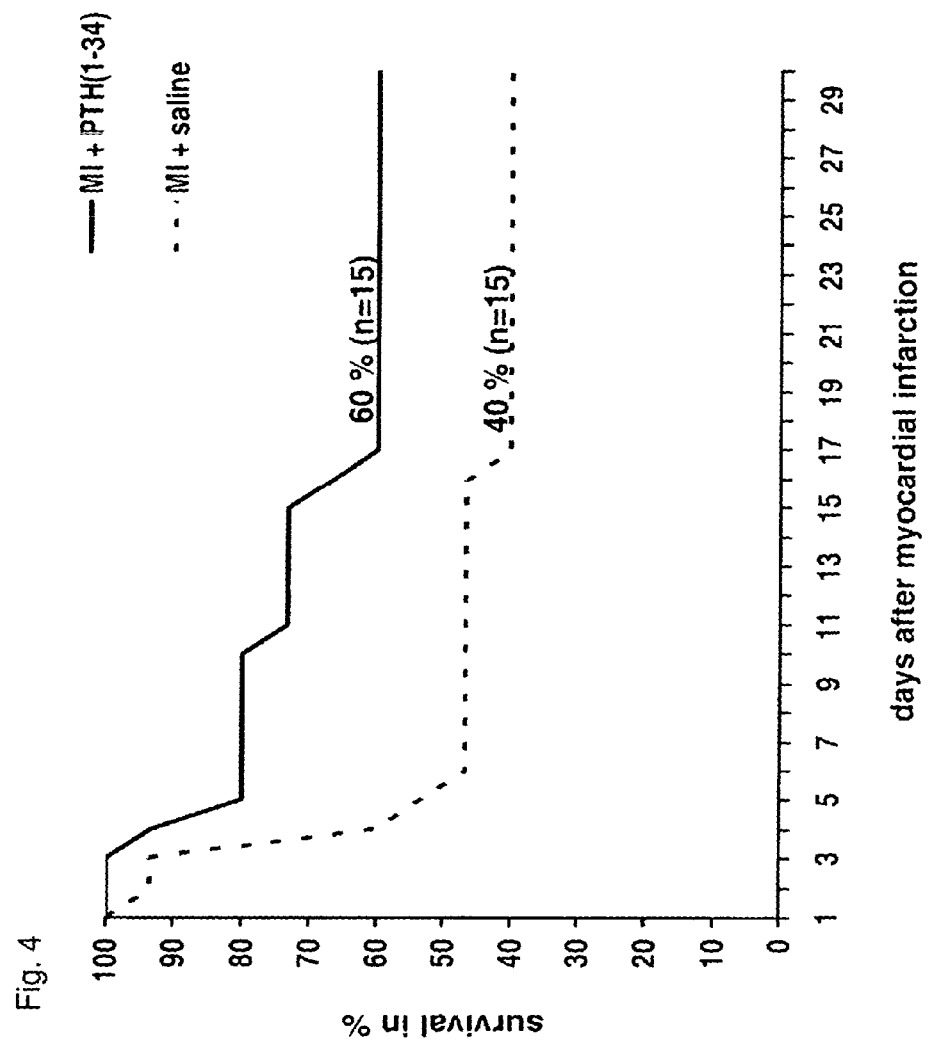

Figure 1
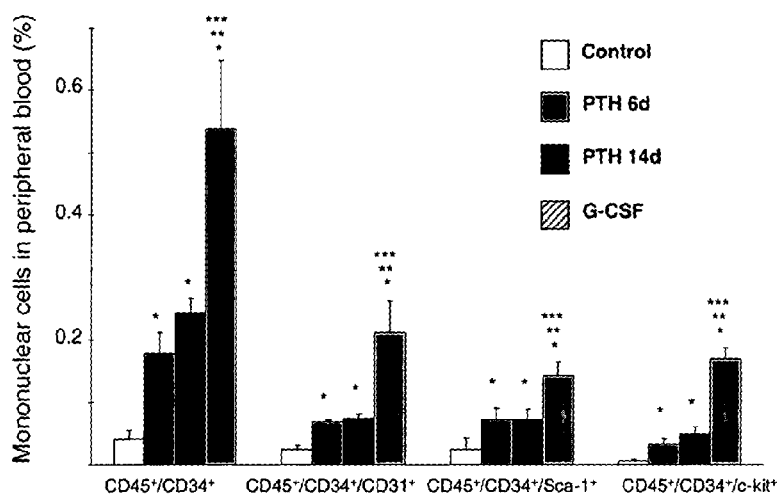
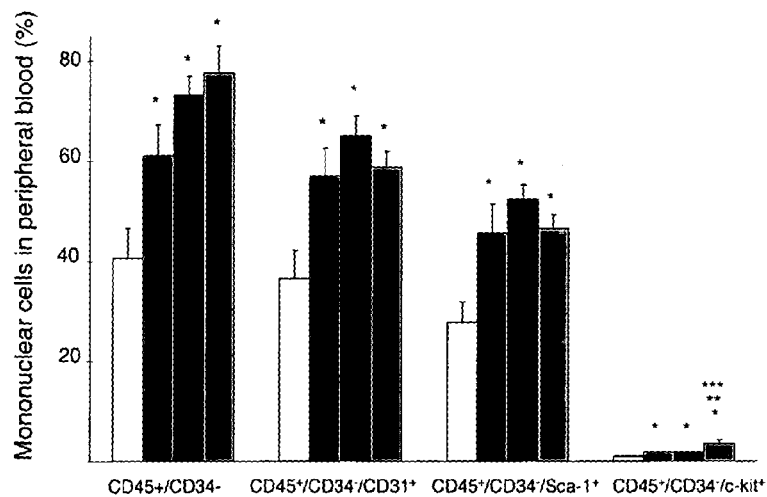

Figure 2
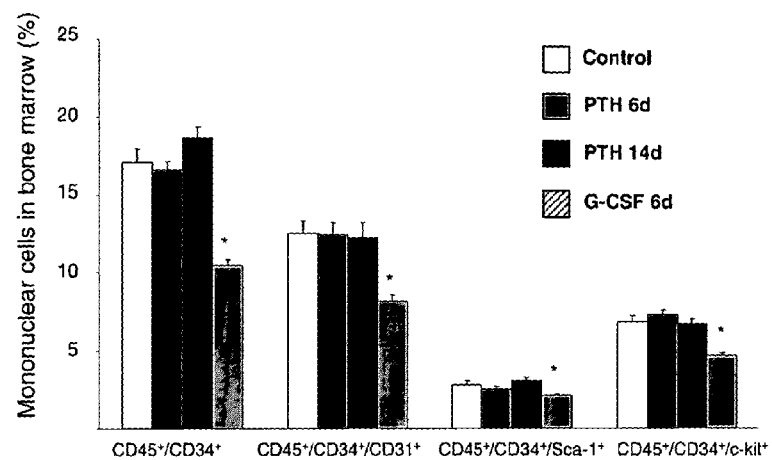
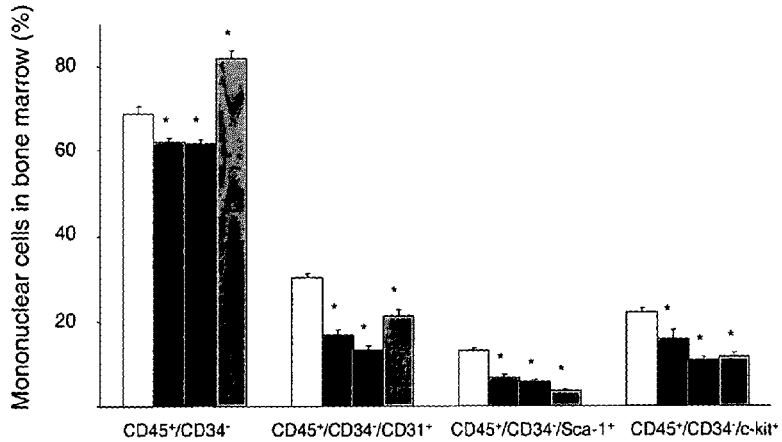

Figure 3
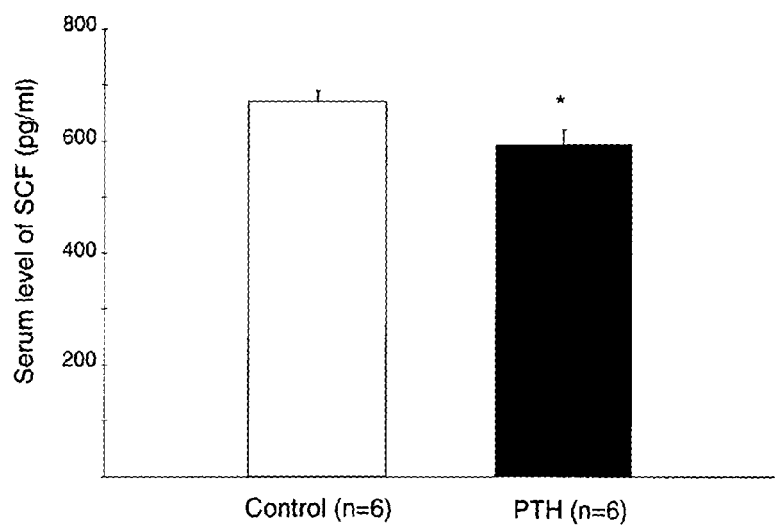
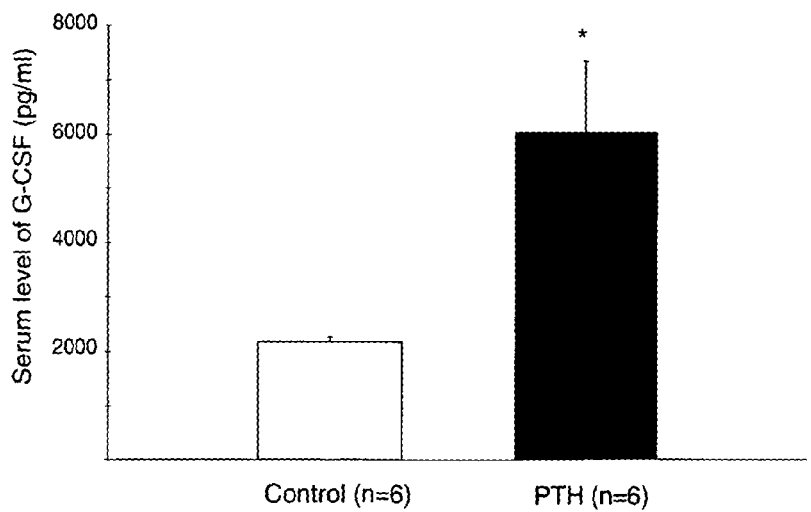

Figure 15
A  pressure volume loops
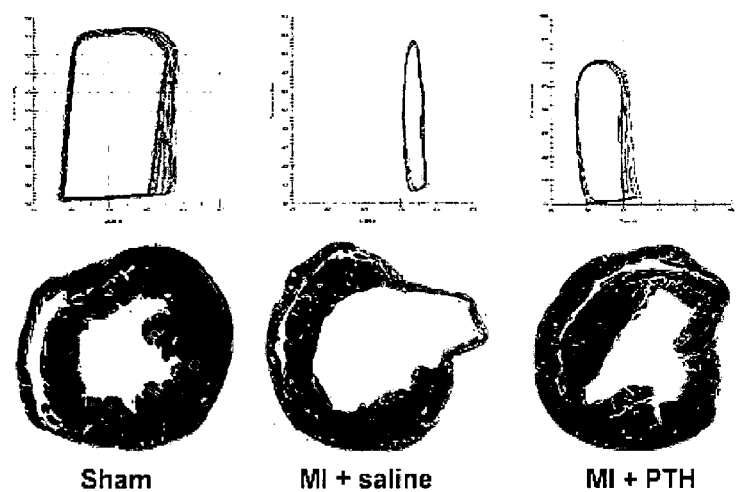
Sham     MI + saline     MI + PTH
B
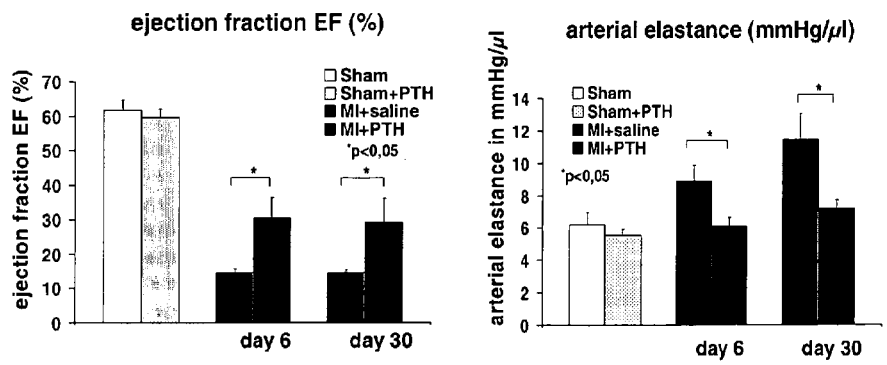

Figure 17
A
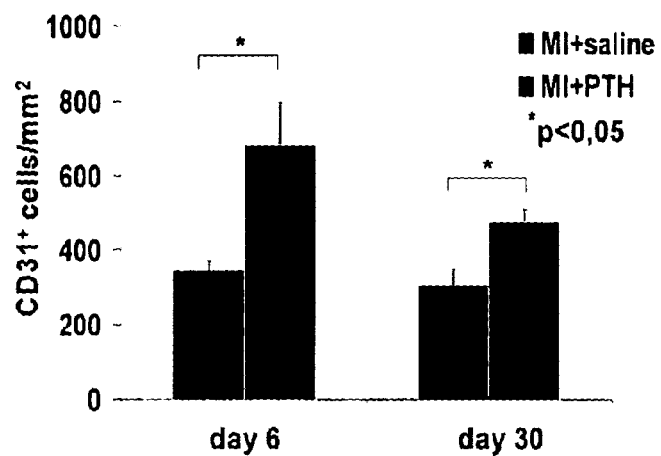
CD31+ vessels at the borderzone of infarction
B
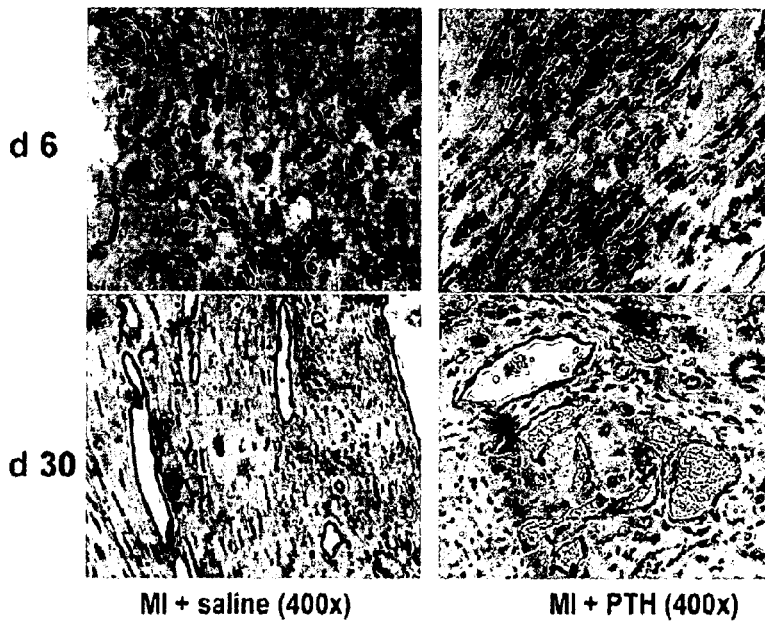

Figure 20
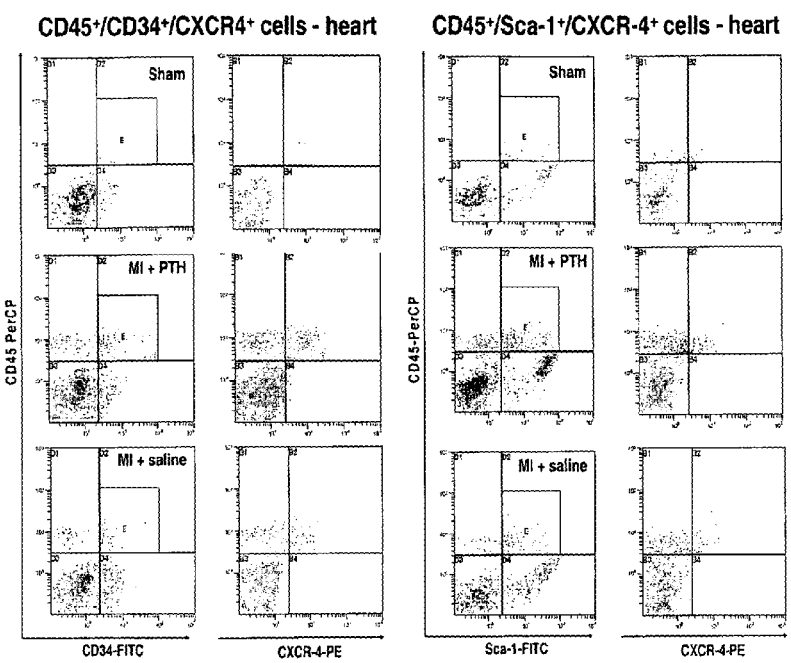
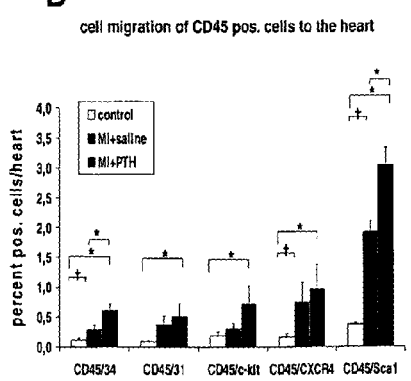
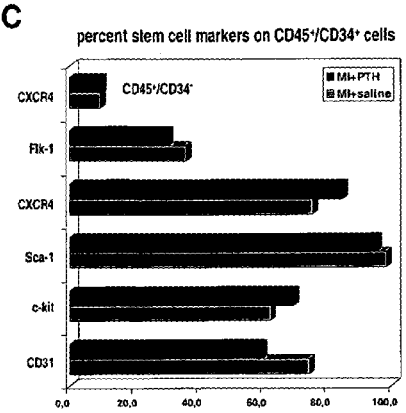

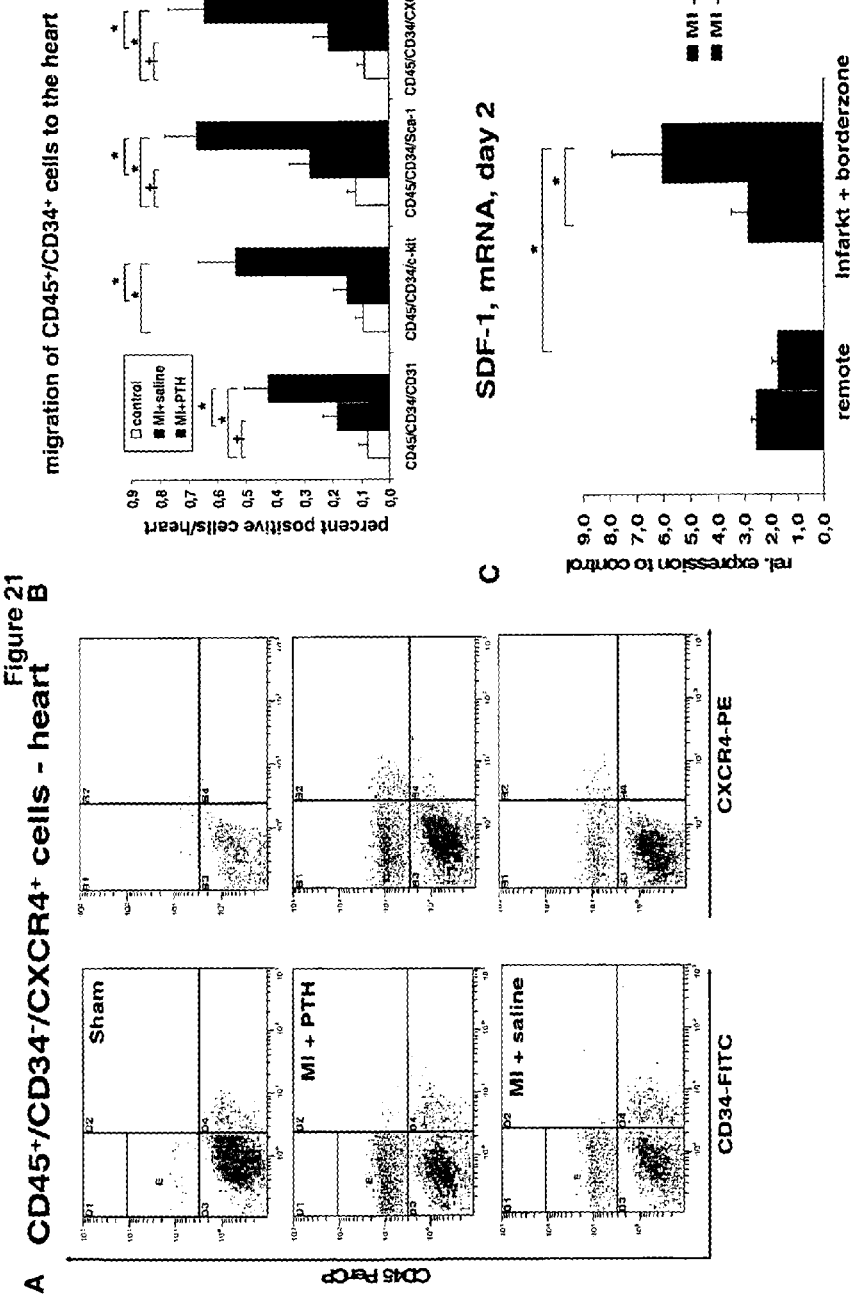

```
SEQUENCE LISTING

<160> NUMBER OF SEQ ID NOS: 7

<210> SEQ ID NO 1
<211> LENGTH: 115
<212> TYPE: PRT
<213> ORGANISM: homo sapiens

<400> SEQUENCE: 1

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30

Val Ser Glu Ile Gln Leu Met His Asn Leu Gly Lys His Leu Asn Ser
        35                  40                  45

Met Glu Arg Val Glu Trp Leu Arg Lys Lys Leu Gln Asp Val His Asn
    50                  55                  60
```

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln
        115

<210> SEQ ID NO 2
<211> LENGTH: 84
<212> TYPE: PRT
<213> ORGANISM: homo sapiens

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 3
<211> LENGTH: 34
<212> TYPE: PRT
<213> ORGANISM: homo sapiens

<400> SEQUENCE: 3

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 4
<211> LENGTH: 139
<212> TYPE: PRT
<213> ORGANISM: homo sapiens

<400> SEQUENCE: 4

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Glu Ile Arg Ala Thr Ser Glu Val Ser Pro Asn Ser Lys Pro
            35                  40                  45

Ser Pro Asn Thr Lys Asn His Pro Val Arg Phe Gly Ser Asp Asp Glu
        50                  55                  60

Gly Arg Tyr Leu Thr Gln Glu Thr Asn Lys Val Glu Thr Tyr Lys Glu
65                  70                  75                  80

Gln Pro Leu Lys Thr Pro Gly Lys Lys Lys Gly Lys Pro Gly Lys
                85                  90                  95

-continued

```
Arg Lys Glu Gln Glu Lys Lys Arg Arg Thr Arg Ser Ala Trp Leu
            100                 105                 110
Asp Ser Gly Val Thr Gly Ser Gly Leu Glu Gly Asp His Leu Ser Asp
        115                 120                 125
Thr Ser Thr Ser Leu Glu Leu Asp Ser Arg
        130                 135

<210> SEQ ID NO 5
<211> LENGTH: 141
<212> TYPE: PRT
<213> ORGANISM: homo sapiens

<400> SEQUENCE: 5

Ala Val Ser Glu His Gln Leu Leu His Asp Lys Gly Lys Ser Ile Gln
1               5                   10                  15
Asp Leu Arg Arg Arg Phe Phe Leu His His Leu Ile Ala Glu Ile His
            20                  25                  30
Thr Ala Glu Ile Arg Ala Thr Ser Glu Val Ser Pro Asn Ser Lys Pro
        35                  40                  45
Ser Pro Asn Thr Lys Asn His Pro Val Arg Phe Gly Ser Asp Asp Glu
    50                  55                  60
Gly Arg Tyr Leu Thr Gln Glu Thr Asn Lys Val Glu Thr Tyr Lys Glu
65                  70                  75                  80
Gln Pro Leu Lys Thr Pro Gly Lys Lys Lys Gly Lys Pro Gly Lys
            85                  90                  95
Arg Lys Glu Gln Glu Lys Lys Lys Arg Arg Thr Arg Ser Ala Trp Leu
            100                 105                 110
Asp Ser Gly Val Thr Gly Ser Gly Leu Glu Gly Asp His Leu Ser Asp
        115                 120                 125
Thr Ser Thr Ser Leu Glu Leu Asp Ser Arg Arg His
        130                 135                 140

<210> SEQ ID NO 6
<211> LENGTH: 173
<212> TYPE: PRT
<213> ORGANISM: homo sapiens

<400> SEQUENCE: 6

Ala Val Ser Glu His Gln Leu Leu His Asp Lys Gly Lys Ser Ile Gln
1               5                   10                  15
Asp Leu Arg Arg Arg Phe Phe Leu His His Leu Ile Ala Glu Ile His
            20                  25                  30
Thr Ala Glu Ile Arg Ala Thr Ser Glu Val Ser Pro Asn Ser Lys Pro
        35                  40                  45
Ser Pro Asn Thr Lys Asn His Pro Val Arg Phe Gly Ser Asp Asp Glu
    50                  55                  60
Gly Arg Tyr Leu Thr Gln Glu Thr Asn Lys Val Glu Thr Tyr Lys Glu
65                  70                  75                  80
Gln Pro Leu Lys Thr Pro Gly Lys Lys Lys Gly Lys Pro Gly Lys
            85                  90                  95
Arg Lys Glu Gln Glu Lys Lys Lys Arg Arg Thr Arg Ser Ala Trp Leu
            100                 105                 110
Asp Ser Gly Val Thr Gly Ser Gly Leu Glu Gly Asp His Leu Ser Asp
        115                 120                 125
Thr Ser Thr Ser Leu Glu Leu Asp Ser Arg Thr Ala Leu Leu Trp
        130                 135                 140
Gly Leu Lys Lys Lys Lys Glu Asn Asn Arg Arg Thr His His Met Gln
```

-continued

```
                145                 150                 155                 160
Leu Met Ile Ser Leu Phe Lys Ser Pro Leu Leu Leu Leu
                165                 170

<210> SEQ ID NO 7
<211> LENGTH: 34
<212> TYPE: PRT
<213> ORGANISM: homo sapiens

<400> SEQUENCE: 7

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala
```

REMEDIES FOR ISCHEMIA

The present invention relates to uses and methods of parathyroid hormone (PTH), preferably PTH (1-34), and/or parathyroid hormone-related peptide (PTHrP), preferably PTHrP (1-34), for recruiting stem cells into tissue suffering from ischemia, wherein said stem cells are preferably capable of repairing and/or regenerating said tissue suffering from ischemia. Accordingly, the uses and methods of the present invention are preferably suitable for the prevention and/or treatment of ischemia. Moreover, the present invention relates to a composition comprising parathyroid hormone (PTH), preferably PTH (1-34), and/or parathyroid hormone-related peptide (PTHrP), preferably PTHrP (1-34), and/or G-CSF or a G-CSF fragment for use as a pharmaceutical composition. In a particular aspect of the invention, a DPP IV antagonist is applied in the uses, methods and/or compositions of the present invention. Also the use of PTH alone or PTHrP alone or in combination with a DPP IV antagonist in the herein disclosed medical and pharmaceutical uses and methods is part of this invention.

Stem Cells

The mobilization of hematopoietic stem cells has become an established method for autologous stem cell transplantation. Under steady-state conditions the number of hematopoietic stem cells is much lower in peripheral blood than in bone marrow. Mobilization of these cells with chemotherapy and/or growth factors made it able to increase the concentration in the peripheral blood, making stem cell transplantation with autologous hematopoietic stem cells from the peripheral blood possible. This method results in a more gentle treatment and a faster hematologic recovery[1]. Besides these findings, in the recent years several studies have shown an increased neovascularisation in ischemic models after mobilizing progenitor cells with cytokines such as granulocyte colony-stimulating factor[2] and granulocyte monocyte colony-stimulating factor[3], growth factors such as vascular endothelial growth factor[4], placental growth factor[5] and erythropoietin[6], chemokines such as stromal cell-derived factor-1[7], hormones such as estrogens[8] and lipid-lowering drugs[9,10] as well as physical activity[11]. Accordingly, this might lead to new therapeutic options for ischemic diseases.

Moreover, cytokine-mediated mobilization of hematopoietic stem cells has become an established method in the field of autologous stem cell transplantation from peripheral blood.

Parathyroid Hormone (PTH)

Parathyroid hormone is well known as one of the two major hormones modulating calcium and phosphate homeostasis. It is responsible for maintaining serum ionized calcium concentrations within a narrow range, through its action to stimulate renal tubular calcium reabsorption and bone resorption. On a more chronic basis, parathyroid hormone also stimulates the conversion of calcidiol to calcitriol in renal tubular cells, thereby stimulating intestinal calcium absorbtion[12-16]. In recent years, the receptor for parathyroid hormone was shown to be expressed in several tissues suggesting more complex functions of this hormone[17,18]. Just recently the influence of parathyroid hormone on the hematopoietic stem cell (HSC) niche in the bone marrow has been shown, where it strengthens survival and self-renewal of hematopoietic stem cells[19]. Zhu[22] suggested that through PTH signalling the expression of N-cadherin and Jag1 is upregulated which strengthens HSC survival and self-renewal through the Notch1-signalling pathway.

In vitro and in vivo, exogenous PTH (1-34) and its structurally related endogenous secreted peptide PTHrP are potent dilators of the arterial bed[30,31]. Moreover, PTH (1-34) dose dependently increases regional myocardial blood flow[31,32]. Recently, it was shown that PTH (1-34) administration in a reperfusion model in pigs after myocardial infarction improved myocardial contractility and myocardial perfusion[32]. Arterial vasodilation is based on the activation of PTH/PTHrP receptor type I[33] which is known to be expressed on smooth muscle cells. PTH/PTHrP receptor activation results in an increase of cAMP production. To summarize, it is known that PTH has cardiovascular functions such as vasodilatation, increased myocardial blood flow, hypotensive effects, myocardial hypertrophy, positive chronotropic and contractility effects. The latter effect is, however, controversially discussed in the art.

Moreover, it has also been observed in clinical studies that the progress of cardiovascular disease may be associated with PTH; see Wing et al. (1984), Contr. Nephrol., Bernardi et al. (1985), Nephron or London et al. (1987), Kidney Int.

Mice lacking the PTH/PTHrP receptor type I die at the midgestational age around day 12 due to abrupt cardiomyocyte necrosis showing the essential role of PTH in the early cardiovascular development. Moreover, PTH (1-34) treatment induced a higher SDF-1 mRNA level in the bone marrow[35].

Parathyroid Hormone Related Peptide (PTHrP)

Parathyroid hormone-related protein (PTHrP) is actually a family of protein hormones produced by most if not all tissues in the body. A segment of PTHrP is closely related to parathyroid hormone, and hence its name, but PTHrP peptides have a much broader spectrum of effects. Parathyroid hormone and some of the PTHrP peptides bind to the same receptor, but PTHrP peptides also bind to several other receptors. PTHrP was discovered as a protein secreted by certain tumors that caused hypercalcemia (elevated blood calcium levels) in affected patients. It was soon shown that the uncontrolled secretion of PTHrP by many tumor cells induces hypercalcemia by stimulating resorption of calcium from bone and suppressing calcium loss in urine, similar to what is seen with hyperparathyroidism. However, it has quickly become apparent that PTHrP had many activities not seen with parathyroid hormone. For example, it is believed in the art that PTHrP causes low blood pressure and tachycardia in connection with paraneoplastic hypercalcemia; see Nichols et al. (1989), Endocrinology.

Ischemic Diseases

Ischemia, is a restriction in blood supply, generally due to factors in the blood vessels, with resultant damage or dysfunction of tissue. Ischemia is a feature of heart diseases, transient ischemic attacks, cerebrovascular accidents, ruptured arteriovenous malformations, and peripheral artery occlusive disease. Thus, ischemia affects almost all organs and tissues. Tissues especially sensitive to inadequate blood supply are the heart, the kidneys, and the brain. Ischemia in brain tissue, for example due to stroke or head injury, causes a process called the ischemic cascade to be unleashed, in which proteolytic enzymes, reactive oxygen species, and other harmful chemicals damage and may ultimately kill brain tissue.

Ischemia of the heart muscle due to a cardiovascular disease, e.g., due to myocardial infarction is a major problem that has to be tackled by modern medicine. Cardiovascular disease is the number one cause of mortality in Western countries and claims approximately 1 million lives each year in the United States. The majority of cardiovascular deaths are due to coronary artery disease (CAD). CAD is a progressive disease that results in a spectrum of clinical manifestations, ranging from asymptomatic atherosclerosis and stable angina to the acute coronary syndromes (i.e., unstable angina, myocardial infarction (MI), and sudden ischemic death). The treatment of choice for acute ST segment elevation MI is either thrombolysis or primary coronary intervention (PCI) when coronary catheterization is immediately accessible. These revascularization strategies are well established in the treatment of acute MI when treatment is initiated very early after onset of infarction (usually within 6 hours).

Despite the fact that hospital mortality after myocardial infarction dropped with improved treatment in the last decade there are more and more patients suffering from the deterioration to cardiac insufficiency over time. Therefore, alternative regenerative strategies are needed to overcome this major problem. Promising data on animal models as well as clinical studies revealed positive effects after transplantation of bone marrow derived cells on cardiac function after MI[32]-[39]. An elegant alternative could be the administration of cardioprotective substances which also have the ability to mobilize and influence stem cells. Previous studies have evidenced that administration of stem cell mobilizing cytokines like G-CSF after myocardial infarction reduces myocardial damage and mortality[35], [40], [41]. Furthermore, first clinical studies have shown a beneficial role of G-CSF treatment on post MI function[42], [43]. Moreover, in recent years it has been demonstrated in different studies that mobilization of bone marrow derived cells is a powerful tool to promote neovascularization in ischemic tissues. Promising data on animal models as well as clinical studies have shown that transplantation or mobilization of bone marrow derived cells show positive effects on cardiac function after myocardial infarction[35]-[39].

Nevertheless, despite many efforts there is still a need for effective means and methods to treat and/or prevent ischemia. In particular, there is a need for economical and/or clinical efficient means and methods for the treatment and/or prevention of ischemia.

Thus, the technical problem of the present invention is to comply with the needs described above. The solution to this technical problem is achieved by providing the embodiments described herein and characterized in the claims.

As detailed herein below and also summarized in the experimental part of this invention, the present invention provides remedies for ischemia, in particular, means, methods and uses for preventing and/or treating ischemia.

Before the present invention is described in detail, it is to be understood that this invention is not limited to the particular methodology, protocols, cell lines, vectors, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" or "the use" includes reference to equivalent steps and methods or uses known to those of ordinary skill in the art that could be modified or substituted for the methods or uses described herein.

Accordingly, in one aspect the present invention relates to the use of parathyroid hormone (PTH) and/or parathyroid hormone-related peptide (PTHrP) for the preparation of a pharmaceutical composition for recruiting stem cells into tissue suffering from ischemia and/or apoptosis. Said stem cells are upon administration of PTH and/or PTHrP believed—without being bound by theory—to be mobilized from the bone marrow so as to be present in the periphery. It is, moreover, assumed that said stem cells are preferably recruited into tissue suffering from ischemia. In addition, it is believed that PTH and/or PTHrP has a direct beneficial effect on cells of tissue suffering from ischemia through binding to the PTH receptor or PTHrP receptor, respectively. Accordingly, it is believed that PTH and/or PTHrP has a beneficial effect on tissue suffering from ischemia due to the effect on stem cells as described herein and/or due to a direct effect on cells of tissue suffering from ischemia.

Another aspect of the present invention is a method of recruiting stem cells into ischemic tissue comprising administering an effective amount of a pharmaceutical composition comprising parathyroid hormone (PTH) and/or parathyroid hormone-related peptide (PTHrP) to a patient in need thereof.

The present invention is based on the surprising finding that stem cells can be recruited from the bone marrow into the periphery, preferably into tissue suffering from ischemia by parathyroid hormone (PTH) or parathyroid hormone-related peptide (PTHrP). Accordingly, the present inventors aimed to define in a murine model system the impact of PTH on stem cells mobilization, vessel growth, post myocardial infarction survival as well as functional parameters of infarcted myocardium 6 days and 30 days after a surgical procedure further detailed herein below and in the appended Example. The data obtained in the murine model with respect to the prevention and/or treatment of ischemia of the heart are generalizable for the prevention and/or treatment of ischemia of other tissues and/or organs as described herein.

The mobilisation of stem cells from bone marrow by cytokine therapy presents an alternative for direct application of stem cells by cardiac catheterization: It seems that mobilised and injected stem cells remain only for a short time in the infarcted myocardium. This could be due to the time course of the myocardial homing capacity post infarction: HSC express the homing receptor CXCR-4 which corresponds to its unique homing factor SDF-1. SDF-1 is upregulated for about 24-48 hours post infarction. Without being bound by theory, this period might be too short for efficient and consistent stem cell homing in human patients. So, efficient and prolonged upregulation of SDF-1 could optimise stem cell therapy after, for example, myocardial infarction.

SDF-1 (CXCL12) is—among others—a substrate for CD26, which is a membrane bound, extracellular dipeptidyl peptidase that splices proteins at their N-terminal end after the amino acid-sequence X-alanine or X-proline. A large number of bone marrow stem cells express CD26 on the cell surface. By blocking the activity of CD26 an increased capacity of transmigration towards an SDF-1 gradient is believed to be achievable.

In combination with cytokine-mobilisation or catheter-based application of stem cells, this might lead to a breakthrough of stem cell therapy in cardiac diseases.

Accordingly, In a further aspect, the present inventors have analyzed the effect of administration of the DPP-IV-inhibitor diprotin A after myocardial infarction in a mouse model. DPP IV is the abbreviation for dipeptidylpeptidase IV and is also referred to as CD26 herein and also in the literature. Dipeptidyl peptidase IV (DPP-IV or CD26) cleaves dipeptides N-terminal after X-Pro/X-Ala and degrades for example the substrates SDF-1 and GLP-1. Dipeptidyl peptidase IV (DPP-IV or CD26) can be inhibited, for example, by diprotin A. The data obtained by the present inventors (see the appended examples and figures, in particular Example 22 and FIG. 14) show that DPP-IV-inhibition via, for example, Diprotin A leads to a significantly improved cardiac function after myocardial infarction in a mouse model. Thus, a DPP IV antagonist (also interchangeably used herein as "DPP IV inhibitor") as defined herein can be applied in the embodiments described herein, i.e. in the uses, methods and/or compositions of the present invention instead of, or together with parathyroid hormone (PTH) and/or parathyroid hormone-related peptide (PTHrP). Accordingly, the combinatory/combinational use of PTH or PTHrP and a DPP IV inhibitor is also envisaged in the embodiments of this invention. The terms Parathyroid hormone (PTH) and/or parathyroid hormone-related peptide (PTHrP) are described in great detail herein below. It will be understood that Diprotin A is of course only an example of a DPP IV antagonist within the meaning of the present invention and, thus, in general, any DPP IV antagonist is contemplated to be applied in the uses, methods and/or compositions of the present invention. DPP IV antagonists are known in the art, e.g., Diprotin A, Vildagliptin or Sitagliptin. DPP IV antagonists are also described, for example, in US2003/0119750, WO 2005/063750, DE-A1 1 010 0053, US 2004/147434, WO 2003/002596, WO 2007/035665, EP 1 743 655, US 2006/270701, US 2006/217428, WO 2005/025554, AU 2003261487, CA 2 471 204

For example, DPP-IV inhibitors like Vildagliptin or Sitagliptin are already approved for clinical use in diabetes mellitus and are thus within the scope of the present invention.

The term "inhibitor" defines in the context of the present invention a compound or a plurality of compounds which interact(s) with DPP-IV such that the cleavage of dipeptides N-terminal after X-Pro/X-Ala is reduced and/or the degradation of, for example, the substrates SDF-1 and GLP-1 is reduced. The term "plurality of compounds" is to be understood as a plurality of substances which may or may not be identical. The plurality of compounds may preferably act additively or synergistically. Said compound or plurality of compounds may be chemically synthesized or microbiologically produced and/or comprised in, for example, samples, e.g., cell extracts from, e.g., plants, animals or microorganisms.

Furthermore, said compound(s) may be known in the art but hitherto not known to be capable of reducing the cleavage of dipeptides N-terminal after X-Pro/X-Ala and/or the degradation of, for example, the substrates SDF-1 and GLP-1 mediated by DPP-IV.

The interaction of the inhibitor with DPP-IV such that the cleavage of dipeptides N-terminal after X-Pro/X-Ala is reduced and/or the degradation of, for example, the substrates SDF-1 and GLP-1 is reduced can, in accordance with this invention e.g. be effected by a reduction of the amount of the DPP-IV in cells, in tissues comprising said cells or subjects comprising said tissues or cells for example by aptamers, antisense oligonucleotides, iRNA or siRNA which specifically bind to the nucleotides sequences encoding said DPP-IV or by ribozymes which specifically degrade polynucleotides which encode DPP-IV; by blocking the binding site of DPP-IV for its substrates; by competitive or allosteric inhibition of the cleavage of dipeptides N-terminal after X-Pro/X-Ala and/or the degradation of, for example, the substrates SDF-1 and GLP-1 or by otherwise reducing or preventing the cleavage of dipeptides N-terminal after X-Pro/X-Ala and/or the degradation of, for example, the substrates SDF-1 and GLP-1, for example by directing antibodies and/or aptamers to DPP-IV and thereby reducing or preventing the cleavage of dipeptides N-terminal after X-Pro/X-Ala and/or the degradation of, for example, the substrates SDF-1 and GLP-1. Thus, an example of an inhibitor of this invention is an antibody, preferably an antibody the binding of which interferes with the cleavage of dipeptides N-terminal after X-Pro/X-Ala and/or the degradation of, for example, the substrates SDF-1 and GLP-1 mediated by DPP-IV; an antisense construct, iRNA, siRNA or ribozyme constructs directed against a transcript or the coding nucleotide sequence of DPP-IV; nucleotide sequences encoding such constructs and compounds which inhibit the cleavage of dipeptides N-terminal after X-Pro/X-Ala and/or the degradation of, for example, the substrates SDF-1 and GLP-1.

The term "reduced" or "reducing" as used herein defines the reduction of the cleavage of dipeptides N-terminal after X-Pro/X-Ala and/or the degradation of, for example, the substrates SDF-1 and GLP-1

For medical treatment it is preferable to use inhibitors that act in a reversible manner and do not block biochemical processes completely, because such drugs can be applied in a dosage that complies with the desired effect.

Accordingly, it is envisaged that the inhibitor of the invention at least reduces the cleavage of dipeptides N-terminal after X-Pro/X-Ala and/or the degradation of, for example, the substrates SDF-1 and GLP-1 as mediated by DPP-IV to 5%, 10%, 20%, 30%, 40%, 50%, 60%, 70%, 80%, 90% or even 100% when compared to the cleavage of dipeptides N-terminal after X-Pro/X-Ala and/or the degradation of, for example, the substrates SDF-1 and GLP-1 that is achieved without the addition of said inhibitor. The reduction will also depend on the dosage and on the way of administration of the inhibitor. The dosage regimen utilizing the inhibitor of the present invention is therefore selected in accordance with a variety of factors including type, species, age, weight, sex and medical condition of the patient; the severity of the condition to be treated; the route of administration; and the particular compound employed. It will be acknowledged that an ordinarily skilled physician or veterinarian can easily determine and prescribe the effective amount of the compound required to prevent, counter or arrest the progress of the condition.

In a preferred embodiment of the use or the methods of the present invention said inhibitor(s) specifically reduce(s) the cleavage of dipeptides N-terminal after X-Pro/X-Ala and/or the degradation of, for example, the substrates SDF-1 and GLP-1 mediated by DPP-IV. The term "specifically reduce(s)" used in accordance with the present invention means that the inhibitor specifically causes a reduction of the cleavage of dipeptides N-terminal after X-Pro/X-Ala and/or the degradation of, for example, the substrates SDF-1 and GLP-1 mediated by DPP-IV but has no or essentially has no significant effect on other cellular proteins or enzymes.

The term "DPP IV antagonist" or "DPP IV inhibitor" when used herein also encompasses an agent or a drug or a compound that inhibits or antagonizes the physiological effect of DPP IV. It also encompasses competitive, non-competitive, functional, non-functional and chemical antagonists which inhibit or antagonize the physiological effect of DPP IV.

Any compound can be tested by methods known in the art for its effect on DPP IV, i.e. whether or not it can act as a DPP IV inhibitor. For example, to measure the activity of DPP-IV, a continuous fluorometric assay can be employed using, e.g. the peptide Gly-Pro-AMC, which is cleaved by the enzyme to release the fluorescent aminomethylcoumarin (AMC). A typical reaction contained 50 pmol/l enzyme, 50 µmol/l Gly-Pro-AMC, and buffer (100 mmol/l HEPES, pH 7.5, 0.1 mg/ml BSA) in a total reaction volume of 100 µl. Liberation of AMC can be monitored using an excitation wavelength of 360 nm and an emission wavelength of 460 nm. The enzyme used in these studies can be soluble, bound or immobilized and is preferably a human protein produced, for example, in a baculovirus expression system. Accordingly, in order to measure a DPP IV inhibiting activity of a compound, such a compound is added to the above described assay and the skilled person can easily monitor whether AMC release is inhibited in comparison to a test reaction in which the compound to be tested is not added.

The present inventors have investigated parathyroid hormone (PTH) and/or a DPP IV antagonist for its potential to mobilize bone marrow derived cells and/or to improve migration and/or homing of stem cells. In fact, it was observed that parathyroid hormone (PTH), which is known as a regulating hormone in calcium and phosphate homeostasis, is an effective agent to mobilize cells from bone marrow so as to be present in the periphery from where said stem cells are—without being bound by theory—due to the action of PTH preferably recruited into ischemic tissues and/or organs.

Accordingly, in order to investigate the effect of parathyroid hormone (PTH) on mobilization of bone marrow derived hematopoietic stem cells mice were treated with parathyroid hormone (PTH) (80 µg/kg/d) for 6 or 14 days. A negative control group was treated with saline, a positive control group with granulocyte-colony stimulating factor (G-CSF) (200 µg/kg/d) for 5 days. Flow cytometry results on distinct subpopulations of $CD45^+/CD34^+$ and $CD45^+/CD34^-$ cells evidenced a significant increase in PTH treated mice (1.5- to 9.8-fold). Compared to G-CSF treatment mobilization of $CD45^+/CD34^+$ cells by PTH is less effective (20-50%) whereas effects on $CD45^+/CD34^-$ cells were similar in both groups. In bone marrow all $CD45^+/CD34^+$ subpopulations remained constant after PTH treatment but decreased after G-CSF treatment. The percentage of $CD45^+/CD34^-$ subpopulations decreased significantly in all groups. In PTH treated mice ELISA results revealed significant increased values of G-CSF (2.8-fold) but not of stem cell factor (SCF). In summary, these results showed that PTH is able to induce mobilization of bone marrow-derived cells.

In particular, the results obtained in these experiments showed an increase of all subpopulations of bone marrow derived cells in the peripheral blood after stimulation with PTH. In the bone marrow the $CD45^+/CD34^+$ subpopulations remained constant whereas the percentage of $CD45^+/CD34^-$ subpopulations decreased after stimulation. Serum levels of G-CSF but not SCF show increased values.

Accordingly, the present invention shows for the first time the role of parathyroid hormone as an effective stimulator for mobilization of bone marrow derived cells. Therefore, PTH is a promising substance for the repair of defect tissues, in particular ischemic tissues via mobilizing bone marrow derived cells as described herein.

Since PTH and PTHrP are closely related, it is believed without being bound by theory, that for the reasons explained before with regard to PTH, also PTHrP is a promising substance for the regeneration and/or repair of defect tissues, in particular ischemic tissues as described herein. Moreover, it is assumed that a combination of PTH and PTHrP has preferably a synergistic effect on the recruitment of stem cells from bone marrow into the periphery, preferably into tissue suffering from ischemia. Thus, a combination of PTH and PTHrP may also be useful for the prevention and/or treatment of ischemia.

In fact, the present inventors when addressing the question whether PTH beside its vasodilating effects regulate the bone marrow stem cell niche, so as to effect repair of tissue, in particular ischemic tissue as described herein, aimed to define survival, functional parameters as well as stem cell mobilization in a murine model of surgically induced myocardial infarction (MI) after treatment with PTH.

For that purpose 12-24 h after ligation of the left anterior descendens (LAD) rat PTH (1-34) was injected once a day for 14 consecutive days. At two time points (day 6 and day 30) after the surgical procedure, pressure volume relationships were investigated in vivo using conductance catheters. Furthermore, infarct size as well as cell proliferation was determined by BrdU and Ki67 incorporation. In addition, stem cell mobilization was analyzed by FACS.

PTH treatment resulted in a significant improvement of survival post MI (60% vs. 40%). FACS data on peripheral blood samples demonstrated stem cell mobilization 6 and 14 days after PTH treatment. Compared to saline, PTH treatment resulted in an improved myocardial function showing comparable values at day 6 (EF: 30% vs. 15%) and day 30 (EF: 29% vs. 15%). Functional improvement was associated with a reduced peripheral resistance at day 6 (Arterial elastance Ea: 6.0 vs. 8.9 mmHg/µl) and day 30 (Ea: 11.4 vs. 7.1 mmHg/µl). Infarct size was reduced at day 30 (23% vs. 33%) but not at day 6 (37% vs. 39%). Histology of PTH treated mice revealed a reduced decline of the thickness of the free LV wall at the two time points investigated (day 6: 0.58 vs. 0.42 mm, day 30: 0.22 vs. 0.13 mm). Therefore, it is believed that PTH administration after myocardial infarction is associated with stem cell mobilization, an improved rate of survival, and a beneficial effect on myocardial function up to 4 weeks after MI.

Of course, these findings are generalizable to other tissues and/or organs suffering from ischemia, since the aforementioned experimental results have been obtained in a model system for ischemia. As described herein, ischemia is a general restriction in blood supply which thus affects many organs and/or tissues which are strictly dependent on a continuous blood flow. Therefore, it is believed that the results obtained in the murine model system described herein are also applicable for preventing and/or treating ischemia of other tissues and/or organs as described herein.

The results and findings for PTH as observed in the murine model system for ischemia are believed to be similar or identical when using PTHrP since PTHrP and PTH are closely related. Thus, also PTHrP is believed to recruit stem cells into tissue suffering from ischemia and, thereby, repairing and/or regenerating tissue suffering from ischemia. Thus, preferably PTHrP is useful for preventing and/or treating ischemia. Moreover, also a combination of PTH and PTHrP is believed to be useful for the prevention and/or treatment of ischemia.

Hence, PTH and/or PTHrP treatment appears to be an interesting, promising combination of direct vasodilating with stem cell modulating effects as described herein, preferably for the treatment and/or prevention of ischemia and/or apoptosis.

The above described results and findings with respect to the recruitment of stem cells into tissue suffering from ischemia and/or apoptosis and for the prevention and/or treatment of ischemia, respectively, which are further described in the appended Examples are even more surprising. This is because, the prior art regarded PTH to be not beneficial in acute myocardial infarction. Namely, Conway et al. (1990), Am. Surg. 8:463-470 repeated earlier studies done by Feola and co-workers (Feola et al. (1985), Circ. Shock 17:163-177 and Feola et al. (1986), Surg. Gynecol. Obstet. 163:523-530) and has come to the conclusion that PTH is not beneficial in the treatment of acute myocardial infarction which causes ischemia and, thus, organ defects. However, as described herein, the present invention discloses and demonstrates herein, in particular in the appended Examples, that PTH is preferably useful in the prevention and/or treatment of ischemia.

To the more, in the work described by Conway et al. (1990), Feola et al. (1985) and Feola et al. (1986), all cited above, occlusion of the LAD of the heart of the mice was only temporarily to study the effect of PTH, while in the experiments done by the present inventors, occlusion of the LAD was permanent. Though this severe burden for the mice which is assumed to cause major ischemia, it is even more surprising that PTH had the beneficial effects described herein and further described in the appended Examples.

When used in the context of the present invention, the term "parathyroid hormone", also abbreviated as "PTH" is sometimes also referred to as "parathormone" encompasses both naturally-occurring and synthetic forms of PTH and other forms of PTH, such as variants, analogs etc. as described herein below. It is to be understood that PTH is a polypeptide.

The term "polypeptide" when used herein means a peptide, a protein, or a polypeptide which are used interchangeable and which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. As mentioned the terms polypeptide and protein are often used interchangeably herein. The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York (1983), pgs. 1-12; Seifter, Meth. Enzymol. 182 (1990); 626-646, Rattan, Ann. NY Acad. Sci. 663 (1992); 48-62. For example, a modified PTH, i.e. [Leu$^{27}$]cyclo (Glu$^{22}$-Lys$^{26}$) PTH (1-31) is a PTH form encompassed by the term PTH.

Naturally-occurring PTH is a secreted 84 amino acid product of the mammalian parathyroid gland that controls serum calcium levels through its action on various tissues, including bone. PTH containing 84 amino acids is designated as PTH 1-84; see G. N. Hendy et al. (1981), Proc. Natl. Acad. Sci. USA 78, 7365; T. Kimura et al. (1983), Biochem. Biophys. Res. Commun. 114, 493; J. M. Zanelli et al. (1985), Endocrinology 117, 1962 or E. Wingender et al. (1989), J. Biol. Chem. 264, 4367. PTH is also disclosed in EP-B1 926 158 or EP-A1 1 059 933. PTH may be obtained by known recombinant or synthetic methods, such as described in U.S. Pat. Nos. 4,086,196 and 5,556,940. When peptide synthesis is adopted, PTH can be obtained by peptide chemical synthesis which is ordinarily conducted. For conducting peptide chemical synthesis, for example, the azide method, the acid chloride method, the azide anhydride method, the DCC method, the activated ester method, the carbon imidazole method or the oxidization-reduction method may be employed.

The term "PTH" when used herein includes a parathyroid hormone which is characterized by having the amino acid sequence shown in SEQ ID NO: 1. SEQ ID NO: 1 shows the human PTH full-length peptide. The full-length peptide contains 115 amino acids. Amino acids 1-25 are believed to belong to a signal sequence, amino acids 26-115 are believed to belong to the PTH proprotein and amino acids 32 to 115 are believed to belong to the parathyroid hormone. Amino acids 32 to 115 of SEQ ID NO: 1 as described herein are regarded to constitute PTH (1-84) shown in SEQ ID NO: 2, wherein amino acid position 32 and 115 of SEQ ID NO: 1 correspond to positions 1 and 84 of PTH, respectively. PTH (1-84) includes PTH (1-34) which corresponds to amino acid positions 32 to 65 of SEQ ID NO: 1. For PTH (1-34) shown in SEQ ID NO: 3 also amino acid position 32 of SEQ ID NO: 1 corresponds to amino acid position 1. The same holds true for the numbering of all PTHs described herein.

Of course, also PTH from mouse (Accession No. NP 065648), rat (Accession No. NP 058740), chicken (Accession No. NP 990783), bovine (Accession No. NP 776379) or other mammals is contemplated to be employed by the uses, methods and compositions of the present application.

The term "PTH" also encompasses variants of PTH. A "variant" of the polypeptide of the present invention encompasses a polypeptide wherein one or more amino acid residues are substituted, preferably conservatively substituted compared to said polypeptide and wherein said variant is preferably able to have PTH activity. Any form of PTH to be employed in the uses, methods and compositions of the present invention has preferably PTH activity which is preferably characterized by the capability of PTH to bind to its receptor. Alternatively, PTH activity can be measured as is known in the art.

Such variants include deletions, insertions, inversions, repeats, and substitutions selected according to general rules known in the art so as have no effect on the activity of the polypeptide of the present invention. For example, guidance concerning how to make phenotypically silent amino acid substitutions is provided in Bowie, Science 247: (1990) 1306-1310, wherein the authors indicate that there are two main strategies for studying the tolerance of an amino acid sequence to change. The first strategy exploits the tolerance of amino acid substitutions by natural selection during the process of evolution. By comparing amino acid sequences in different species, conserved amino acids can be identified.

These conserved amino acids are likely important for protein function. In contrast, the amino acid positions where substitutions have been tolerated by natural selection indicate that these positions are not critical for protein function. Thus, positions tolerating amino acid substitution could be modified while still maintaining biological activity of the protein. The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244: (1989) 1081-1085.) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require non-polar side chains, whereas few features of surface side chains are generally conserved.

The invention encompasses polypeptides having a lower degree of identity but having sufficient similarity so as to perform one or more of the functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al. above, such conservative substitutions are likely to be phenotypically silent. Additional guidance concerning which amino acid changes are likely to be phenotypically silent are found in Bowie, Science 247: (1990) 1306-1310.

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided below.

| For Amino Acid | Code | Replace with any of: |
|---|---|---|
| Alanine | A | D-Ala, Gly, beta-Ala, L-Cys, D-C$_3$s |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-As |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(0), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Infoliuaties and Genome Projects, Smith, D M., ed., Academic Press, New York, 1993; Informafies Computer Analysis of Sequence Data, Part 1, Griffin, A. M., and Griffin, H. G., eds., Humana Press, New Jersey, 1994; Sequence Analysis in Molecular Biology, von Heinje, G., Academie Press, 1987; and Sequence Analysis Primer, Gribskov, M. and Devereux, eds., M Stockton Press, New York, 1991.

Alternatives in the form of PTH variants incorporate from 1 to 5 amino acid substitutions that improve PTH stability and half-life, such as the replacement of methionine residues at positions 8 and/or 18 with leucine or other hydrophobic amino acid that improves PTH stability against oxidation and the replacement of amino acids in the 25-27 region with trypsin-insensitive amino acids such as histidine or other amino acid that improves PTH stability against protease.

The term "PTH" also encompasses fragments of PTH (1-84) characterized as having 84-n amino acids, wherein n is an integer from 1 to 56. Namely, PTH fragments contain sequential deletions from the C-terminal e.g. fragments desirably contain at least the first 28 N-terminal residues. The term "PTH" preferably encompasses PTH (1-28), PTH (1-31), PTH (1-34), PTH (1-37), PTH (1-38) and PTH (1-41). Particularly preferred is PTH (1-34) which is also known as teriparatide; see, for example S. H. Doppelt et al. (1981), Calcif. Tissue Int. 33, 649; R. Podbesek et al. (1983), Endocrinology 112, 1000; G. N. Kent et al. (1985), Clin. Sci. 68, 171; R. L. McKee and M. P. Caulfield (1989), Peptide Res. 2, 161; S. C. Lee and A. F. Russell (1989), Biopolymers 28, 1115; J. Reeve et al. (1990), Br. Med. J. 301, 314 or W. Neugebauer et al. (1994), Int. J. Peptide Protein Res. 43, 555

The term "PTH" also encompasses polypeptides which are at least 50, 60, 70, 80, 90, 95 or 99% identical to either the amino acid sequence shown in SEQ ID NO: 1, 2 or 3, respectively. Further guidance with respect to the calculation of percent identity is provided herein below and is applicable to the aforementioned embodiment.

The term "PTH" also encompasses analogs of PTH as disclosed in EP-A1 651 765, EP-A1 1 123 401, EP-A 1 772 448 or EP-A2 1 276 767 (in particular, the analogs listed in the Tables therein).

The term "parathyroid hormone-related peptide", also abbreviated as "PTHrP" may sometimes be referred to as "parathormone-related peptide" encompasses both naturally-occurring or synthetic forms of PTHrP and other forms of PTHrP, such as variants, analogs etc. as described herein below. It is to be understood that PTHrP is a polypeptide.

Parathyroid hormone-related protein (PTHrP) is actually a family of protein hormones produced by most if not all tissues in the body. Its identification and characterization is, for example, disclosed in EP-B1 273 928. A segment of PTHrP is closely related to parathyroid hormone, and hence its name, but PTHrP peptides have a much broader spectrum of effects. Parathyroid hormone and some of the PTHrP peptides bind to the same receptor, but PTHrP peptides also bind to several other receptors.

PTHrP was discovered as a protein secreted by certain tumors that caused hypercalcemia (elevated blood calcium levels) in affected patients. It was soon shown that the uncontrolled secretion of PTHrP by many tumor cells induces hypercalcemia by stimulating resorption of calcium from bone and suppressing calcium loss in urine, similar to what is seen with hyperparathyroidism. However, it quickly becomes apparent that PTHrP had many activities not seen with parathyroid hormone.

PTHrP is encoded by a single gene that is highly conserved among species. It should probably be described as a polyhormone, because a family of peptide hormones are generated by alternative splicing of the primary transcript and through use of alternative post-translational cleavage sites. To make matters even more complex, some cells appear to use alternative translational initiation codons to produce forms of the protein that are targeted either for secretion or nuclear localization. The PTHrP preprohormone consisting of 139 amino acids is, for example, processed to yield 3 bioactive peptides, i.e. a PTH-like peptide (1-36), a midregion peptide (38-94) and an osteostatin peptide (107-139).

The diverse activities of PTHrP result not only from processing of the precursor into multiple hormones, but from use of multiple receptors. It is clear that amino-terminal peptides of PTHrP share a receptor with parathyroid hormone, but they also bind to a type of receptor in some tissues that does not bind parathyroid hormone. Moreover, it is almost certain that the midregion and osteostatin peptides bind other, unique receptors.

In addition to the secreted forms of this hormone, there is considerable evidence that a form of PTHrP is generated in some cells that is not secreted and, via nuclear targeting sequences, is translocated to the nucleus, where it affects nuclear function. The consequences of this "intracrine" mode of action are not yet well characterized, but may modulate such important activities as programmed cell death.

PTHrP is secreted from a large and diverse set of cells, and during both fetal and postnatal life. Among tissues known to secrete this hormone are several types of epithelium, mesenchyme, vascular smooth muscle and central nervous system. Although PTHrP is found in serum, a majority of its activity appears to reflect paracrine signaling.

One thing to recognize about PTHrP is that its name is inadequate to describe its activities. Like parathyroid hormone, some of the effects of PTHrP result from its effects on transepithelial fluxes of calcium, but many of its actions have nothing to do with calcium homeostasis. Most prominently, PTHrP peptides exert significant control over the proliferation, differentiation and death of many cell types. They also play a major role in development of several tissues and organs.

The term "PTHrP" also includes a peptide which is characterized by having the amino acid sequence shown in SEQ ID NO: 4, 5, 6 or 7.

The term "PTHrP" also encompasses variants of PTHrP. The same embodiment for variants as described herein above for PTH variants applies to PTHrP variants, mutatis mutandis. Preferably, the term "PTHrP" encompasses PTHrP (1-34) or PTHrP (1-36). Also preferred is any fragment of PTHrP characterized as having 84-m amino acids, wherein m is an integer from 1 to 50 as long as said fragment contains PTHrP (1-34) shown in SEQ ID NO:7. PTH (1-34) is, for example, described in B. E. Kemp et al. (1987), Science 238, 1568; J. M. Moseley et al. (1987), Proc. Natl. Acad. Sci. USA 84, 5048; L. J. Suva et al. (1987), Science 237, 893 or V. Paspaliaris et al. (1995), Bone 16, 141S. Any form of PTHrP to be employed in the uses, methods and compositions of the present invention has preferably PTHrP activity which is preferably characterized by the capability of PTHrP to bind to its receptor. Alternatively, PTHrP activity can be measured as is known in the art.

The term "PTHrP" also encompasses polypeptides which are at least 50, 60, 70, 80, 90, 95 or 99% identical to either the amino acid sequence shown in SEQ ID NO: 4, 5, 6 or 7, respectively. Further guidance with respect to the calculation of percent identity is provided herein and is applicable to the aforementioned embodiment.

The term "PTHrP" also includes analogs of PTHrP as disclosed in EP-A1 948 541.

A PTH or PTHrP peptide from any organism is envisaged to be employed in the uses, methods and compositions of the present application. A PTH or PTHrP peptide from any organism can, for example, be identified by using sequence comparisons and/or alignments by employing means and methods known in the art, preferably those described herein and comparing and/or aligning (a) known PTH or PTHrP to/with a sequence suspected to be a PTH or PTHrP.

For example, when a position in both of the two compared sequences is occupied by the same amino acid monomer subunit (for instance, if a position in each of two polypeptides is occupied by a lysine), then the respective molecules are identical at that position. The percentage identity between two sequences is a function of the number of matching or identical positions shared by the two sequences divided by the number of positions compared×100. For instance, if 6 of 10 of the positions in two sequences are matched or are identical, then the two sequences are 60% identical. By way of example, the amino acid sequences ALTSPY and AYTIWY share 50% homology (3 of the 6 total positions are matched). Generally, a comparison is made when two sequences are aligned to give maximum homology and/or identity. Such alignment can be provided using, for instance, the method of Needleman, J. Mol Biol. 48 (1970): 443-453, implemented conveniently by computer programs such as the Align program (DNAstar, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354-352, Nat. Biomed. Res. Foundation, Washington, D.C. (1978).

Of course, the terms "PTH" and "PTHrP" do not only stand for a polypeptide having an amino acid sequence, but also stand for the nucleic acid molecules having nucleotide sequences encoding the amino acid sequences of PTH and PTHrP, respectively.

The term "nucleic acid molecule" when used herein encompasses any nucleic acid molecule having a nucleotide sequence of bases comprising purine- and pyrimidine bases which are comprised by said nucleic acid molecule, whereby said bases represent the primary structure of a nucleic acid molecule. Nucleic acid sequences include DNA, cDNA, genomic DNA, RNA, synthetic forms, for example, PNA, and mixed polymers, both sense and antisense strands, or may contain non-natural or derivatized nucleotide bases, as will be readily appreciated by those skilled in the art. The polynucleotide of the present invention is preferably composed of any polyribonucleotide or polydeoxyribonucleotide, which may be unmodified RNA or DNA or modified RNA or DNA. For example, the polynucleotide can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. The polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, the term "nucleic acid molecules" embraces chemically, enzymatically, or metabolically modified forms.

In the context of the present invention, also nucleic acid sequences which hybridize to a nucleic acid sequence encoding a PTH or PTHrP are envisaged.

Moreover, also nucleic acid sequences which are at least 65%, more preferably 70%, 75%, 80%, 85%, 90%, 95%, 97%, 98% or 99% identical to a nucleic acid sequence encoding a PTH or PTHrP are envisaged.

Accordingly, the term "hybridizing sequences" preferably refers to sequences which display a sequence identity of at least 65%, even more preferably at least 70%, particularly preferred at least 80%, more particularly preferred at least 90%, even more particularly preferred at least 95% and most preferably at least 97, 98% or 99% identity with a nucleic acid sequence as described above.

Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Such fragments may represent nucleic acid sequences as described herein. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., at least 65% identity, preferably, at least 70-95% identity, more preferably at least 95%, 96%, 97%, 98% or 99% identity), when compared and aligned for maximum correspondence over a window of comparison, or over a designated region as measured using a sequence comparison algorithm as known in the art, or by manual alignment and visual inspection. Sequences having, for example, 65% to 95% or greater sequence identity are considered to be substantially identical. Such a definition also applies to the complement of a test sequence.

Those having skill in the art will know how to determine percent identity between/among sequences using, for example, algorithms such as those based on CLUSTALW computer program (Thompson Nucl. Acids Res. 2 (1994), 46734680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands.

For example, BLAST2.0, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments. BLAST produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules.

Moreover, the term "PTH" or "PTHrP" also encompasses nucleic acid molecules the sequence of which is degenerate in comparison with the sequence of an above-described nucleic acid molecules. When used in accordance with the present invention the term "being degenerate as a result of the genetic code" means that due to the redundancy of the genetic code different nucleotide sequences code for the same amino acid.

Of course, the present invention also envisages the complementary strand to the aforementioned and below mentioned nucleic acid molecules if they may be in a single-stranded form.

Preferably, the nucleic acid molecule according to the invention may be any type of nucleic acid, e.g. DNA, genomicDNA, cDNA, RNA or PNA (peptide nucleic acid).

For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

The DNA may, for example, be genomic DNA or cDNA. The RNA may be, e.g., mRNA. The nucleic acid molecule may be natural, synthetic or semisynthetic or it may be a derivative, such as peptide nucleic acid (Nielsen, Science 254 (1991), 1497-1500) or phosphorothioates. Furthermore, the nucleic acid molecule may be a recombinantly produced chimeric nucleic acid molecule comprising any of the aforementioned nucleic acid molecules either alone or in combination.

The term "recruiting stem cells" when used herein means that stem cells are mobilized from places within an animal or human body, e.g. from bone marrow so as to be present in the periphery, from where said stem cells can preferably migrate to other places within the animal or human body, preferably into tissue suffering from ischemia. The term "tissue" suffering from ischemia includes cells, tissue and/or organs of the animal or human body which suffer from ischemia.

Moreover, the term "recruiting stem cells" as used herein also refers to the ability to attract stem and/or progenitor cells from, e.g. the bone marrow preferably towards tissue suffering from ischemia. Without being bound by theory, it is assumed that SDF-1 is required to induce stem cell homing to injured tissue, e.g., myocardium. Stem cells may bind SDF-1 via their CXCR4 receptor (Petit (2002) Nat. Immunol. 687-694). The aforementioned process is also understood as "homing". The term "homing" as used herein refers to the stem and/or progenitor cells' innate ability to travel preferably to the right place in the body. Preferably, said stem and/or progenitor cells travel to sites where organ defects/dysfunction caused by ischemia have taken/take place.

Preferably, said stem cells are selected from the group consisting of CD34(+)/CD45(+) and CD34(−)/CD45(+) cells, each in combination with the subpopulations CD31(+), Sca-1(+) or C-kit(+), multipotent adult progenitor cells (MAPC), endothelial progenitor cells (EPC) characterized by CD34(+), CD45(+), CD31(+), side population cells (SP) and lineage-negative stem cells, lin(−), c-kit(+). The aforementioned stem cells may additionally express CXCR4. The stem cells and/or progenitor cells are characterized by using FACS analysis as described in the appended Examples.

Notably, it was observed by the present inventors that administration of PTH does not cause a depletion of stem cells in the bone marrow, but a very efficient mobilization and a stabilization of stem cells as is described in the appended Examples and shown in the Figures. In particular, it was observed that stem cells which express c-kit are efficiently mobilized (5-fold higher in comparison to a control). The stem cells as described herein repair and/or regenerate tissue suffering from ischemia. The terms "repairing" and "regenerating" as used herein relates to restore at least partially the former conditions of the defect organ tissue.

The indication "(+)" and "(−)" refer to results obtained by flow cytometry (FACS) analysis. (+) or "positive" means that a defined protein, such as CD45, CD34 or CD31, etc. is expressed on the surface of an analyzed cell, such as a stem cell or progenitor cell, etc. (−) or "negative" means that a defined protein, such as CD34, CD31 etc. is not expressed on the surface of an analyzed cell, such as a stem cell or a progenitor cell, etc.

In accordance with the present invention the term "pharmaceutical composition" relates to a composition comprising PTH and/or PTHrP. In some embodiments described herein, said pharmaceutical composition also comprises GM-CSF (granulocyte macrophage colony stimulating factor), SCF (stem cell factor), IL-3 (interleukin-3) and/or IL-6 (interleukin-6), erythropoietin (EPO) or a fragment of the aforementioned compounds. In some embodiments, said pharmaceutical composition also comprises G-CSF or a G-CSF fragment or statins or thiolactones. In a further embodiment, said pharmaceutical composition also comprises a DPP IV antagonist/inhibitor. It has also been observed that physical exercise is beneficial for mobilizing stem cells. Accordingly, it is envisaged by the present invention that the medical uses and methods may be accompanied by physical exercise and any other measure which is suitable to mobilize stem cells.

A pharmaceutical composition of the present invention comprises a therapeutically effective amount of PTH and/or PTHrP and, optionally, a pharmaceutically acceptable carrier. As mentioned above, said pharmaceutical composition may also comprise one or more of the aforementioned compounds, e.g., GM-CSF, SCF, IL-3, IL-6, EPO, VEGF, a DPP IV antagonist, statins or thiolactones. As detailed herein, these factors may also be employed in combination in the herein disclosed (medical or pharmaceutical) uses and methods of this invention. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the aforementioned compounds, preferably in purified form, together with a suitable amount of carrier so as to provide the form for proper administration to the patient. The formulation should suit the mode of administration.

Preferably, the pharmaceutical composition of the present invention is suitable for administration to a patient. In the context of the present invention the term "patient" means an individual in need of a treatment, preferably in need of a treatment of a tissue suffering from ischemia. Preferably, the patient is a vertebrate, even more preferred a mammal, particularly preferred a human.

In another preferred embodiment, the composition is formulated in accordance with routine procedures as a pharmaceutical composition adapted for intravenous administration to mammals, preferably vertebrates and more preferably human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. Effective doses may be extrapolated from dose-response curves derived from in vitro or animal model test systems. The precise dose to be employed in the formulation will also depend on the route of administration, and the seriousness of the disease or disorder should be decided according to the judgement of the practitioner and each patient's circumstances. Moreover, for example, the following factors concerning the precise dose may also be taken into account: patient's size, body surface area, age, sex, general health, and other drugs being administered concurrently.

Therefore, it is well known in the art that the dosage regimen will be determined by the attending physician and clinical factors. Proteinaceous pharmaceutically active matter may be present in amounts between 1 ng and 10 mg/kg body weight per dose; however, doses below or above this exemplary range are envisioned, especially considering the aforementioned factors.

Regimes known in the art to be capable of mobilizing increased numbers of bone-marrow derived stem cells into the blood circulation are commonly known in the art.

The dosage regimen of the pharmaceutical composition is to be administered to the patient ranges preferably from 0.1 to 200, 0.1 to 150 or 0.1 to 100 µg per kg body weight, more preferably from 1 to 100 µg per kg body weight, even more preferably from 1 to 90, 1 to 80, 1 to 70, 1 to 60, 1 to 50, 1 to 40, 1 to 30, 1 to 20, 1 to 10 or 1 to 5 µg per kg body weight d. s. c. over a period of at least 1 day, preferably at least 2 days, more preferably at least 3 days, even more preferably at least 4 days, particularly preferred at least 5 days, even more particularly preferred at least 6 days, 10 days, 14 days, 21 days, 28 days or 30 days. However, any other suitable dosage regimen is envisaged which may be determined as described herein.

The administration of the candidate agents of the present invention can be done in a variety of ways, including, but not limited to, orally, subcutaneously, intravenously, intranasally, intrabronchially, transdermally, intranodally, intradermally, intrarectally, intraperitoneally, intramuscularly, intrapulmonary, intraocularly, vaginally, rectally or topically. Where necessary, the composition may also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration In a particularly preferred embodiment the pharmaceutical composition is administered subcutaneously.

In another preferred embodiment the pharmaceutical composition is administered via routes of administration as described supra and infra.

As mentioned herein, the aforementioned embodiments of pharmaceutical compositions of the present invention also pertain to pharmaceutical compositions comprising, apart from PTH and/or PTHrP, G-CSF, GM-CSF (granulocyte macrophage colony stimulating factor), SCF (stem cell factor), IL-3 (interleukin-3) and/or IL-6 (interleukin-6), EPO, VEGF or a fragment of the aforementioned compounds, statins, thiolactones and/or a DPP IV antagonist. This embodiment applies, mutatis mutandis, for the herein disclosed (pharmaceutical and/or medical) uses and methods. Accordingly, also the combinatory/combinational uses of theses factors and antagonists are envisaged The term "G-CSF" (granulocyte colony stimulating factor) as used herein relates to a G-CSF polypeptide/polypeptides which is/are well known in the art; e.g., as G-CSF; trade name: Neupogen® (Filgrastim, commercially available from Amgen) or Granocyte® (Lenograstim, commercially available from Chugai Pharma). The amino acid sequence of G-CSF is described, e.g., in Nagata (1986) Nature 319:415-418. It is known that G-CSF has 174 amino acid residues, however, variants thereof are known and are also encompassed by the term "G-CSF" as described infra. For example, a G-CSF polypeptide having an additional methionine residue at its N-terminus is known. The function of G-CSF can be tested by methods known in the art, for example, described in PCT/EP2004/012036.

Said term also encompasses G-CSF polypeptides from preparations well known in the art, either from natural sources or preferably produced by recombinant means. Multiple forms of natural or recombinant human, mouse or rat G-CSF are known in the art. It is envisaged that the G-CSF or fragment thereof used in the context of the present invention is of pharmaceutical grade suitable for administration to patients as described infra.

Said term also encompasses G-CSF polypeptides comprising an amino acid sequence at least 70%, 80%, 90%, 95%, 97% or 99% identical to the G-CSF polypeptide which is known in the art and has preferably G-CSF activity as described in PCT/EP2004/012036.

The term "G-CSF fragment" when used in the context of the present invention means fragments of G-CSF polypeptides having G-CSF activity. The amino acid sequence of G-CSF and of corresponding variants is known in the art and published in Nagata (1986), Nature 319:415-418. Accordingly, said G-CSF fragments comprise portions of 5, 10, 15, 20, 25, 30, 35, 40, 45, 50, 60, 70, 80, 90, 100, 110, 120, 130, 140, 150, 160 or 170 amino acid residues of the G-CSF protein. Preferably said fragments are biologically active fragments, i.e. fragments which have G-CSF activity. For example, said fragments are capable to, e.g., mobilize multipotent stem cells, improve cardiac function or reduce mortality after acute myocardial. Particularly preferred G-CSF activity can be determined by its ability to induce colony formation, as reported in the literature by Bodine (1993), *Blood* 82:445-55; Bodine (1994), *Blood* 84, 1482-91.

Moreover, also variants of G-CSF are envisaged. Accordingly, G-CSF variants are such variants as described in the context of PTH or PTHrP variants.

The terms "treatment" and "treating" are used herein to generally mean obtaining a desired pharmaceutical and/or physiological effect. Preferably, the effect is therapeutic in terms of partially or completely curing ischemia. The term "treatment" as used herein covers any treatment of tissue suffering from ischemia and/or organ defects and/or dysfunction caused by ischemia in a mammal, particularly a vertebrate and more preferably a human, and includes regenerating and/or repairing suffering from ischemia and/or organ or tissue dysfunction. Thus, the pharmaceutical composition of the present invention is preferably suitable for the prevention and/or treatment of ischemia.

The term "prevention" or "preventing" when used herein means to obtain a protective effect on a tissue which is already suffering from ischemia so as to prevent further damage and/or a protective effect on a tissue which is at a risk of suffering from ischemia.

Accordingly, the pharmaceutical composition of the present invention for the purpose of treating and/or preventing ischemia may preferably be administered to a subject who is at a risk of ischemia and/or who already suffers from ischemia. Thus, the pharmaceutical composition of the present invention may preferably be administered to a subject who is diagnosed to be at a risk of ischemia and/or who already suffers from ischemia.

The term "ischemia" as used herein relates to a condition that may occur in any tissue and/or organ that is suffering a lack of oxygen supply and/or supply with metabolites which occurs when there is an imbalance between oxygen supply and demand, due to inadequate perfusion, e.g., caused by atherosclerosis, restenotic lesions, anemia, stroke or clogged arteries just to name a few, that leads to insufficient oxygen to tissues such as, for example, the heart or brain. However, also medical interventions such as the interruption of the blood flow, e.g., during bypass surgery may lead to ischemia. Said term also encompasses the two most common types of ischemia; i.e. cardiac ischemia and cerebral ischemia. Cardiac ischemia includes a broad variety of conditions, from silent ischemia to stable or unstable angina to myocardial infarction (AMI or "heart attack"). Cerebral ischemia includes prolonged cerebral ischemic syndromes to completed stroke or cerebral infarction. However, ischemia is not limited to the aforementioned organs or tissues, respectively, since it may occur in any organ that is suffering a lack of oxygen supply and/or supply with metabolites.

In the context of the present invention, ischemia causes organ dysfunction and/or organ defects.

The term "surgical or interventional procedure" as used herein relates to a surgical and/or interventional procedure which is suitable to improve organ function, to improve blood flow in defect organ tissue and/or to induce revascularization as thrombolysis (either systemic or local via catheter delivery), balloon angioplasty, stenting, coronary, carotid or peripheral bypass surgery, endatherectomy or ventriculo-coronary stenting.

The term "administered" means administration of a therapeutically effective dose of a pharmaceutical composition of the present invention. Preferably, said therapeutically effective dose is administered to a patient who has tissue suffering from ischemia. Particularly preferred said therapeutically effective dose is administered to a patient suffering from organ defects and/or dysfunction caused by ischemia.

By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The uses, methods and compositions of the present invention are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above.

The attending physician and clinical factors will determine the dosage regimen as described herein. A typical dose can be, for example, in the range of 0.001 to 1000 µg; and as described supra however, doses below or above this exemplary range are envisioned, especially considering the aforementioned factors.

The dosages are preferably given once, twice, trice, four times or five times a day for the period of 1, 2, 3, 4, 5, 6, 7, 8, 9, 10, 11, 12, 13, 14, 21, 28 or 30 days, however, during progression of the treatment the dosages can be given in much longer time intervals and in need can be given in much shorter time intervals, e.g., daily divided into multiple applications. If the regimen is a continuous infusion, it should also be in the range of 1 µg to 10 mg units per kilogram of body weight per minute, respectively. Progress can be monitored by periodic assessment. It is also envisaged that the pharmaceutical compositions are employed in co-therapy approaches, i.e. in co-administration with other medicaments or drugs, for example other drugs for preventing, treating and/or ameliorating ischemia. It is also preferred that the pharmaceutical composition of the present invention is co-administered with GM-CSF (granulocyte macrophage colony stimulating factor), SCF (stem cell factor), IL-3 (interleukin-3) and/or IL-6 (interleukin-6), EPO, VEGF or a fragment thereof, statins, thiolactones and/or with a DPP IV antagonist. Preferably, the pharmaceutical composition of the present invention is co-administered with G-CSF or a G-CSF fragment and/or with a DPP IV antagonist. This means that PTH and/or PTHrP and G-CSF or G-CSF fragment and/or a DPP IV antagonist may be administered in combination with one or more of the aforementioned substances.

When co-administration is envisaged, it is self-explanatory that two or more substances as described herein, e.g., PTH and/or PTHrP and G-CSF or PTH and/or PTHrP and a DPP IV antagonist can be administered simultaneously, sequentially or separately from each other.

In a preferred embodiment of the invention the pharmaceutical composition of the present invention is to be administered before a surgical or interventional procedure. The term "before said surgical or interventional measure" when used in the context of the present invention means that the pharmaceutical composition of the present invention is to be administered before one day, preferably two days, more preferably three days and even more preferably four or five days of said surgical or interventional measure, for example, to prevent ischemic disease as described herein.

In another further preferred embodiment of the invention the pharmaceutical composition of the present invention is to be administered during a surgical or interventional procedure.

The term "during said surgical or interventional measure" when used in the context of the present invention means that the pharmaceutical composition of the present invention is to be administered during a surgical or interventional procedure.

In an also preferred embodiment of the invention the pharmaceutical composition of the present invention is to be administered after a surgical or interventional procedure.

The term "after said surgical or interventional measure" when used in the context of the present invention means that the pharmaceutical composition is to be administered preferably immediately after said surgical or interventional measure. Particularly preferred, it is to be administered preferably immediately after said surgical or interventional measure or, alternatively, after at least 1 hour, preferably after at least 6, 12, 24 or 48 hours. Moreover, as described above, the pharmaceutical composition of the present invention, after it has been administered before, during or after a surgical or interventional measure is further administered for the period of time as described above so as to preferably prevent and/or treat ischemia.

Preferably, the ischemia treated with the pharmaceutical composition of the present invention is selected from the group consisting of myocardial ischemia, cerebral ischemia, renal ischemia, liver ischemia, peripheral muscle tissue ischemia, retinal ischemia and spinal cord ischemia. As described supra, ischemia may occur in any tissue and/or organ suffering from a lack of oxygen and/or metabolites for a prolonged time which results in organic defects. The term "organ defect" as used herein relates to dysfunctional myocardium, brain, kidney, liver, peripheral muscle, retina or spinal cord defects. Said organ defects are caused by myocardial ischemia, e.g., due to heart failure, hypertension, coronary artery disease (CAD), myocardial infarction, thrombo-embolic events, trauma and/or surgical procedures; cerebral ischemia, e.g., due to trauma, stroke, thrombo-embolic events, malformation of blood-supplying vessels, multi-infarct disease, cerebral hemorrhage, surgical and/or interventional measures; renal ischemia, e.g., due to thrombo-embolic events, atherosclerosis, malformation of blood-supplying vessels, trauma and/or surgical procedures;

liver ischemia, e.g., due thrombo-embolic events, malformation of blood-supplying vessels, trauma and/or surgical procedures; peripheral muscle tissue ischemia, e.g., is caused by thrombo-embolic events, atherosclerosis, malformation of blood-supplying vessels, trauma and/or surgical procedures; retinal ischemia, e.g., is caused by thrombo-embolic events, malformation of blood-supplying vessels, trauma and/or surgical procedures; and spinal cord ischemia, e.g., is caused by thrombo-embolic events, atherosclerosis, malformation of blood-supplying vessels, trauma and/or surgical procedures.

It is particularly preferred that the myocardial ischemia which is treated with the pharmaceutical composition of the present invention is caused by heart failure, hypertension, coronary artery disease (CAD), myocardial infarction, thrombo-embolic events, trauma and/or surgical procedures.

It is also particularly preferred that the cerebral ischemia which is treated with the pharmaceutical composition of the present invention is caused by trauma, stroke, thrombo-embolic events, malformation of blood-supplying vessels, multi-infarct disease, cerebral hemorrhage, surgical and/or interventional measures.

In still another embodiment it is particularly preferred that the renal ischemia which is treated with the pharmaceutical composition of the present invention is caused by thrombo-embolic events, atherosclerosis, malformation of blood-supplying vessels, trauma and/or surgical procedures.

In a furthermore particularly preferred embodiment it is envisaged that the liver ischemia or retinal ischemia which is treated with the pharmaceutical composition of the present invention is caused by thrombo-embolic events, malformation of blood-supplying vessels, trauma and/or surgical procedures.

A still particularly preferred aspect of the present invention is that the peripheral muscle tissue ischemia or spinal cord ischemia which is treated with the pharmaceutical composition is caused by thrombo-embolic events, atherosclerosis, malformation of blood-supplying vessels, trauma and/or surgical procedures.

In a further aspect the present invention relates to a composition comprising PTH and/or PTHrP and/or G-CSF or a G-CSF fragment for use as a pharmaceutical composition or medicament. All embodiments mentioned herein with respect to the uses and methods of PTH and/or PTHrP apply to said composition, mutatis mutandis.

In a still further aspect the present invention relates to a composition comprising PTH and/or PTHrP and/or a DPP IV antagonist.

In another still further aspect the present invention relates to a composition comprising PTH and/or PTHrP and/or a DPP IV antagonist and/or any of the compounds mentioned herein, e.g., GM-CSF, SCF, IL-3, IL-6, statins, thiolactones and/or EPO.

In the following, the findings observed in the murine model with respect to stem cell mobilization are summarized: in our study we examined the potency of PTH to mobilize bone marrow derived cells and investigated the changes in the composition of cells in bone marrow after administration of PTH. Furthermore, we analysed the serum levels of cytokines as possible effectors.

The main findings are: 1) PTH induced the mobilization of bone marrow derived cells. The mobilizing effect affected almost all investigated cell types, thus seems not to be cell type specific. 2) After administration of PTH, in bone marrow a decrease of all subtypes of $CD45^+CD34^-$ cells occurred, whereas the subtypes of $CD45^+CD34^+$ cells remained constant. 3) G-CSF treatment led to a more effective mobilization of $CD45^+CD34^+$ cells and has a similar effect on $CD45^+$ $CD34^-$ cells. 4) In contrast to PTH treated mice G-CSF treatment led to a significant decrease of all investigated subtypes of $CD45^+CD34^+$ and $CD45^+CD34^-$ cells. 5) Stimulation with PTH led to increased serum levels of G-CSF and decreased levels of SCF.

Recently, Calvi et al. demonstrated a connection between PTH and the hematopoietic system. In their study they found an increase of hematopoietic stem cells in the bone marrow after administration of PTH in wild-type animals. Furthermore, survival after bone marrow transplantation in lethally irradiated mice has been shown to be markedly improved after stimulation with PTH[19]. The changes of bone marrow derived cells in number and composition in peripheral blood were not investigated and remained to be elucidated. In our study, we show for the first time an increase of bone marrow derived cells in peripheral blood after PTH administration. Characterizing these cells, we found an increase of both $CD45^+/CD34^+$ and $CD45^+/CD34^-$ subpopulations in peripheral blood, indicating that different subtypes of hematopoietic stem cells were mobilized by PTH. The increase of these cells occurred already after 6 days of stimulation with PTH. There was a slight but no further significant increase after 14 days of stimulation, suggesting the maximum effect was reached within this time frame. The mobilization did not specifically affect distinct cell types.

However, the influence of PTH on cells within the bone marrow seemed to be more specific. Our results showed a decrease of all investigated subtypes of $CD45^+/CD34^-$ cells indicating that these cells were released from bone marrow into peripheral blood. However, $CD45^+/CD34^+$ subtypes remained constant and did not change after stimulation. Calvi et al. described the strengthening effect of PTH on survival and self-renewal of hematopoietic stem cells through Notch1/Jagged1 ligation. PTH signalling upregulates the expression of Jagged1 by osteogenic stromal cells activating Notch1 signaling pathway in hematopoietic stem cells[19]. PTH stimulation also increases the expression level of N-cadherin on osteoblasts[20]. N-cadherin-mediated adhesion may link to the Wnt-LEF-1-Notch1 pathway through β-catenin signaling[21, 22]. Our results indicate that these mechanism may only effect on $CD45^+/CD34^+$ cells resulting in a constant level of these cells in bone marrow.

Several cytokines like G-CSF, SCF, VEGF or SDF-1 are known to stimulate bone marrow causing a release of stem cells into the circulation[2, 4, 7]. To investigate the function of PTH as a stimulus for the endogenous release of mobilizing cytokines as a possible mechanism of increased bone marrow derived cells in the peripheral blood after PTH stimulation, we measured serum levels of G-CSF and SCF, factors employed in several studies aiming to mobilize stem cells[2, 23-26]. After administration of PTH we found a strong increased concentration of G-CSF, whereas a slight but not significant decrease of SCF was detectable. Osteoblasts, that are among other structural cells in the hematopoietic stem cell niche, can be activated by PTH and are able to produces growth factors[27-29]. Our data suggest an indirect mobilizing effect of PTH by stimulating osteoblasts to produce cytokines such as G-CSF. SCF is negative regulated by PTH, however the pathway and function is not yet known and remains to be elucidated.

To investigate if the mobilizing effect of PTH is solely an indirect effect caused by the endogenous release of G-CSF, we treated healthy mice with G-CSF and investigated the same subtypes of cells. Interestingly different pattern of mobilization are shown. G-CSF treatment resulted in a stronger effect on mobilization of $CD45^+/CD34^+$ cells, whereas the effect on $CD45^+/CD34^-$ cells was comparable with PTH treatment, suggesting a more specific effect of G-CSF on CD34+ cells. Investigating the cell pattern in bone marrow after stimulation with G-CSF, a different effect of G-CSF was shown likewise. G-CSF treatment did not show a stabilizing effect on CD45+/CD34+ cells, but resulted in a significant decrease of these cell in bone marrow as a sign of cell release without self-renewal. G-CSF and PTH treatment caused a decrease of CD45+/CD34− cells in bone marrow at comparable levels, but with different intensities on different subtypes. Besides the indirect effect of PTH through endogenous G-CSF the results suggest an independent effect of PTH on bone marrow derived cells. Our study shows for the first time the ability of PTH to mobilize bone marrow derived cells. The mechanism for cell mobilization might occur in part through the endogenous release of cytokines such as G-CSF but not SCF. In contrast to G-CSF, PTH shows a stabilizing effect in bone marrow. This effect of PTH seems to act especially on CD34+ cells.

To summarize, the main findings of the present invention with respect to the murine model for ischemia are: 1) a beneficial effect on myocardial function and survival which was related to 2) an increased mobilization of stem cells into peripheral blood 3) a reduced arterial load and a 4) a beneficial effect on postinfarct remodelling characterized by a higher rate of endothelial proliferation and a reduced decline of the LV anterior wall.

PTH Treatment Induces Stem Cell Mobilization into the Peripheral Blood

Recently, Calvi et al.[34] showed that PTH is involved in the regulation of the bone marrow stem cell pool[36]. Overexpression of the hPTH/PTHrp receptor under control of the osteoblast specific α1(I) collagen promoter led to an increase of Sca-1 and c-kit positive stem cells in the bone marrow. The increase in the number of stem cells was mediated via jagged1 Notch signaling leading to a proliferation of primitive stem cells. Furthermore, PTH (1-34) is known to induce the expression and secretion of G-CSF and MMP-9 known inductors of stem cell mobilization[47, 48]. Therefore, we measured the amount of stem cell mobilization after PTH treatment. We could demonstrate to our knowledge for the first time that the daily application of PTH (80 µg(kg/d) was sufficient to increase various populations of CD45 positive stem cell in the peripheral blood. Compared to G-CSF treatment the effect is only moderate. As an increase in the amounts of stem cells in the peripheral blood is correlated to improved myocardial revascularization after MI we investigated the effects of PTH on vascularization.

Furthermore, our results demonstrate a stable effect of PTH (80 µg/kg/d) application on the mobilization of various populations of CD34, CD31, Sca-1 and c-kit positive bone marrow stem cells into the peripheral blood. Until now PTH was not known as a mobilizer of stem cells. Calvi (loc. cit) showed that PTH is involved in the regulation of the bone marrow stem cell niche: Overexpression of the hPTH/PTHrp receptor under control of the osteoblast specific α1(I) collagen promoter led to an increased proliferation of Sca-1 and c-kit positive stem cells in the bone marrow. The rise in the number of stem cells was mediated via jagged1 Notch signaling leading to a pronounced proliferation of primitive cells. However, the mobilization of stem cells by PTH application might reflect a new concept of niche treatment and has not been described so far. Possible mechanisms involved in the PTH induced mobilization could be the increased expression and secretion of G-CSF, SDF and MMP-9 which are known inductors of stem cell mobilization and stem cell homing.

PTH Treatment after MI Improves Long Term Survival and Partially Restores Myocardial Function Our results showed that PTH treatment after MI is related to beneficial effects on survival and global myocardial function over a time period of 4 weeks. Reduction of mortality and improvement of myocardial function was related to a reduced decline of the left ventricular wall and a positive effect on the peripheral arterial resistance. Previously, it was shown that PTH (1-34) administration intravenously (1 U/kg/min) starting 30 minutes after coronary occlusion in dogs exerted a tissue-sparing effect on the myocardium, restored LV function, and prevented the development of cardiogenic shock in a short term manner[47]. More recently, PTH (1-34) treatment was shown to increase myocardial blood flow by reducing coronary artery resistance in pigs in normal and stunned myocardium after intracoronary infusion of PTH (1-34) in a cumulative dose between 12 and 18 µg[32]. However the effect of an intermittent application of PTH after MI was not studied yet. In our study the application of 80 µg/kg/d of PTH resulted in a significant reduction of arterial resistance at day 6 and at day 30 suggesting early vasorelaxing effects in the arterial system including the coronary vasculature. As the highest mortality appeared in the early 6 days after MI this data might be related to others showing a prevention from cardiogenic shocks after PTH treatment[47]. Moreover, we found a reduced decline of the left ventricular wall reducing myocardial wall stress.

Furthermore, our results (see FIGS. 15, 16 and 17) showed beneficial effects of postinfarct PTH treatment on survival and global myocardial function over a time period of 4 weeks. Reduction of mortality and improvement of myocardial function was related to an increased mobilization and migration of CD45+/Sca-1+ and CD45+/CD34+ stem cells to the ischemic heart which could explain the increased VEGF and IGF-1 expression. As VEGF and IGF-1 are known growth factors to enhance neovascularization and reduce the rate of apoptosis this might result in a reduced decline of the left ventricular wall and a smaller infarct scar. Moreover, our data showed a reduced arterial afterload reflected by a reduced arterial elastance at day 6 and day 30. In vitro and in vivo, exogenous PTH (1-34) and it's structurally related endogenous secreted peptide PTHrP are known dilators of the arterial vessel bed. Arterial vasodilatation is based on the activation of PTH/PTHrP receptor type I which is known to be expressed on smooth muscle cells: Upon receptor activation, PTH results in an increase of cAMP production resulting in a decrease of Calcium influx which results in vasodilatation. In this context, PTH (1-34) treatment was shown to increase myocardial blood flow by reducing coronary artery resistance in pigs and rats in normal and stunned myocardium after intracoronary infusion of PTH (1-34) in a cumulative dose between 12 and 18 µg. Another experimental study which subjected male Sprague-Dawley rats to permanent middle cerebral artery occlusion showed, that PTHrP (1-34) peptide treatment significantly decreased cortical infarct size up to 47%. Moreover, it was shown previously that PTH (1-34) administration intravenously (1 U/kg/min) starting 30 minutes after coronary occlusion in dogs exerted a tissue-sparing effect on the myocardium, restored LV function, and prevented the development of cardiogenic shocks in a short term manner. However, the effect of an intermittent application of PTH after MI was not studied yet in a long term manner. In our study the application of 80 µg/kg/d of PTH resulted in a significant reduction of arterial resistance at day 6 and at day 30 suggesting early vasorelaxing effects in the arterial system including the coronary vasculature.

The Impact of PTH (1-34) on Angiogenesis and Cell Survival is Mediated Via the VEGF and IGF-1 Axis.

We investigated the effects of PTH treatment on IGF-1 expression in the infarcted heart.

The binding of IGF-1 to its cell surface receptor (IGF-1R) activates the receptor's intrinsic tyrosine kinase activities, which results in the phosphorylation of the insulin receptor substrates (IRS-1 and IRS-2). Tyrosine-phosphorylated IRSs interact with cytoplasmic proteins with src homology 2 (SH2) domains, such as phosphatidylinositol 3-kinase (PI3K). PI3K activation then leads to the transduction of the functional effects of IGF-1, such as enhanced glucose transport, enhanced cardiomyocyte contractility, and the inhibition of programmed cell death (apoptosis). Furthermore, it was also shown that cardiac remodelling after myocardial infarction is impaired in IGF-1 deficient mice[54]

The mobilization and transfusion of CD34+ bone marrow cells contributes to enhanced neovascularization. Isolated CD34+ blood and bone marrow cells express and secret angiogenic growth factors including VEGF, HGF and IGF-1. As we demonstrate (see FIGS. 18 and 19) a PTH induced migration of CD45+/CD34+ cells to the heart the accumulation of these angiogenic cells could explain the higher expression levels of VEGF-A, VEGF-R1 and IGF-1 receptor in the area of infarction. In this regard we found a significantly increased angiogenesis accompanied by a pronounced expression of VEGF-A and VEGF-R1 in the infarct and borderzone after PTH treatment. However, it is not undoubtedly clear that the increased expression of the proangiogenic factors VEGF-A und VEGF-R1 is a direct effect of PTH or results from mobilized infiltrated blood cells secreting VEGF protein. Immunostaining of hearts 2 and 6 days after MI revealed a high number of leucocytes and monocytes in the granulation tissue which stained positive for VEGF protein supporting the thesis that angiogenic factors have been carried to the site of ischemia. Moreover, it was shown that cardioprotective c-kit+ cells are derived from the bone marrow and act on ischemic myocardium by enhanced neovascularization through angiogenic cytokines like VEGF-A. Recently, it was detected that 7 days after MI a twice increased expression of VEGF after transplantation of GFP+/CD34+ cells into the area of infarction. Moreover, it was shown that the VEGFR1 is a functional receptor on monocyte/macrophage and neutrophils which could be recruited to sides of ischemia by VEGF-A. The VEGFR1-expressing monocyte/macrophages were not able to incorporate into vascular structures but could release angiogenic factors like VEGF-A and induce neovascularization. Another source for the enriched growth factor expression could be the enhanced migration of CD45+/Sca-1+ cells after PTH application. Some PTH treated mice also showed a pronounced accumulation of CD45-/Sca-1+ but this effect was not consistent (data no shown). Recently, Wang et al. described a Sca-1/CD31-positive cell population isolated from the heart which showed an increased neovascularization as main reason for an improved cardiac function after transplantation into ischemic hearts. Isolated cardiac Sca-1 positive cells showed an 8 fold increase of growth factors like VEGF, SDF-1 and IGF-1 when compared to adult cardiac myocytes identifying a possible source of angiogenic factors. Another recent publication shows the differentiation potential of Sca-1 positive embryonic stem cells into functional endothelial cells via activation of HDAC3, accelerating re-endothelialization of injured arteries and reducing neointima formation.

Accordingly, our data show that PTH induces the SDF-1 dependent migration of CD45+/CD34+ and CD45/Sca-1 stem cells which release angiogenic growth factors like VEGF and IGF-1 to promote angiogenesis and anti-apoptotic cell death.

On the other side the direct influence of PTH on neovascularization has only poorly been investigated. Previously, it was shown that PTHrP (1-34) dose-dependently increased capillary formation of endothelial cells on a collagen gel matrix. Moreover, PTH was reported to stimulate VEGF expression in human osteoblast-like cells in vitro. Another work showed a correlation of PTH serum levels and VEGF protein in explanted parathyroid glands transplanted into rats subcutaneously. Another known factor which is secreted from infiltrated blood cells is IGF-1. Our experimental data showed that the IGF-1 receptor protein was upregulated basically on cardiomyocytes at the borderzone at day 2 and at day 6 which was associated with an increased amount of neovascularization and a reduced number of apoptotic cardiomyocytes. The binding of IGF-1 to its cell surface receptor (IGF-1R) activates the receptor's intrinsic tyrosine kinase activities, which results in the phosphorylation of the insulin receptor substrates (IRS-1 and IRS-2). Tyrosine-phosphorylated IRSs interact with phosphatidylinositol 3-kinase (PI3K). PI3K activation then leads to the transduction of the functional effects of IGF-1, such as enhanced neovascularization, enhanced cardiomyocyte contractility, and the inhibition of programmed cell death (apoptosis). In contrast, IGF-1 deficient mice showed an impaired cardiac remodeling after myocardial infarction whereas overexpression of IGF-1 in mice protects from myocyte death after infarction, attenuating ventricular dilation, wall stress, and cardiac hypertrophy. In cultured cardiomyocytes, IGF-1 increased VEGF mRNA and protein expression by 2 fold and recently it was shown that IGF-1 regulates VEGF expression and secretion via HIF-1-dependent and -independent pathways. IGF-1 stimulated VEGF promoter activity was PI3-K/Akt/mTOR dependent. In our experiments IGF-1 receptor was highly expressed basically on cardiomyocytes at the infarct borderzone. As IGF-1 mRNA was also upregulated this could mean a higher sensitivity of borderzone cardiomyocytes to cardioprotective IGF-1 effects like reduced apoptosis and increased neovascularization.

PTH Induced the Migration of CD45/Sca-1 and CD45/CD34/CXCR4 Positive Stem Cells to the Heart In our experiments (see FIGS. 20 and 21) we demonstrate that PTH application resulted in a significant change in the cardiac stem cell niche reflected by the enhanced migration of CD45/Sca-1 and especially CD45/CD34 positive stem cells 48 hours after myocardial ischemia. Subanalysis of the CD45/CD34 stem cell fraction revealed a high expression of the homing factor receptor CXCR4 and other stem cell markers like CD31, c-kit and Sca-1. Nearly 80-90% of the CD45/CD34 positive cardiac cells co-expressed the CXCR4 receptor on their surface strongly suggesting a SDF-1-CXCR4 dependent homing mechanism. In contrast, the subset of CD45+/CD34neg cells only expressed 10% CXCR4 on their surface indicating a CXCR4-SDF-1 independent mechanism of cell migration to the heart. The relevance for the increased homing of the CD34+/CXCR4+ cell subset is supported by our finding that the homing factor SDF-1α is upregulated in the ischemic myocardium 48 hours after PTH treatment. However, the homing of CD45/CD34/CXCR4 positive cells was also seen in saline treated and sham operated animals. The migration was less pronounced especially in sham operated mice and was related to a reduced SDF-1 expression 48 hours after MI (compared with PTH treatment) showing a positive relation between SDF-1 expression and the migration of CD45/CD34/CXCR4 positive stem cells to the heart.

Concerning this matter SDF-1α overexpression in a chronic model of cardiac ischemia led to an increased infiltration of CD34 and c-kit positive stem cells to the heart but the CXCR4 fraction was not analyzed. An 80% increased homing of intravenous infused genetically marked Lin− bone marrow cells to the heart 48 hours after MI was shown. Administration of AMD3100, which specifically blocks binding of SDF-1 to its endogenous receptor CXCR4, diminished the bone marrow derived cell recruitment after MI by 64%. However, in this study only the homing of an infused subpopulation of Lin− cells was quantified. The data of this invention show cell migration to the heart after MI: The accumulation of CD45/CD34/CXCR4 positive cells in the heart was not related to a special treatment modality indicating a common mechanism of cell migration for CD34/CXCR4 positive cells in a SDF-1 dependent manner. In contrast and surprisingly, the CD45$^+$/CD34$^-$ cell fraction revealed a weak CXCR4 expression and, accordingly. another mechanism of cell migration triggered by ICAM/VCAM and chemokines, like TNF-α or interleukins.

In summary and as documented herein, PTH treatment after myocardial infarction resulted in the mobilization and migration of stem cells and preservation of cardiac function by increased angiogenesis and cell survival via VEGF-A and IGF-1 mediated mechanisms which could be explained by an enhanced migration of angiogenic CD45/CD34/CXCR4 positive stem cells. As PTH (1-34) has already been clinically used in patients with osteoporosis to increase bone mineral density, parathyroid hormone might be an interesting supplement or alternative to other stem cell modulating agents like G-CSF or GM-CSF in ischemic heart disease.

The aforementioned results and considerations are envisaged to be applicable as regards PTHrP or a combination of PTH and PTHrP. Accordingly, these results and considerations may be generalizable insofar as PTH and/or PTHrP is/are useful for recruiting of stem cells from the bone marrow into the periphery and, further, is/are useful for the prevention and/or treatment of ischemia.

LITERATURE

1. Jansen, J., Hanks, S., Thompson, J. M., Dugan, M. J. & Akard, L. P. Transplantation of hematopoietic stem cells from the peripheral blood. *J Cell Mol Med* 9, 37-50 (2005).
2. Orlic, D. et al. Mobilized bone marrow cells repair the infarcted heart, improving function and survival. *Proc Natl Acad Sci USA* 98, 10344-10349 (2001).
3. Takahashi, T. et al. Ischemia- and cytokine-induced mobilization of bone marrow-derived endothelial progenitor cells for neovascularization. *Nat Med* 5, 434-438 (1999).
4. Asahara, T. et al. VEGF contributes to postnatal neovascularization by mobilizing bone marrow-derived endothelial progenitor cells. *Embo J* 18, 3964-3972 (1999).
5. Hattori, K. et al. Placental growth factor reconstitutes hematopoiesis by recruiting VEGFR1(+) stem cells from bone-marrow microenvironment. *Nat Med* 8, 841-849 (2002).
6. Heeschen, C. et al. Erythropoietin is a potent physiologic stimulus for endothelial progenitor cell mobilization. *Blood* 102, 1340-1346 (2003).
7. Hattori, K. et al. Plasma elevation of stromal cell-derived factor-1 induces mobilization of mature and immature hematopoietic progenitor and stem cells. *Blood* 97, 3354-3360 (2001).
8. Iwakura, A. et al. Estrogen-mediated, endothelial nitric oxide synthase-dependent mobilization of bone marrow-derived endothelial progenitor cells contributes to reendothelialization after arterial injury. *Circulation* 108, 3115-3121 (2003).
9. Dimmeler, S. et al. HMG-CoA reductase inhibitors (statins) increase endothelial progenitor cells via the PI 3-kinase/Akt pathway. *J Clin Invest* 108, 391-397 (2001).
10. Vasa, M. et al. Increase in circulating endothelial progenitor cells by statin therapy in patients with stable coronary artery disease. *Circulation* 103, 2885-2890 (2001).
11. Laufs, U. et al. Physical training increases endothelial progenitor cells, inhibits neointima formation, and enhances angiogenesis. *Circulation* 109, 220-226 (2004).
12. Brown, E. M. Four-parameter model of the sigmoidal relationship between parathyroid hormone release and extracellular calcium concentration in normal and abnormal parathyroid tissue. *J Clin Endocrinol Metab* 56, 572-581 (1983).
13. Brown, E. M. Mechanisms underlying the regulation of parathyroid hormone secretion in vivo and in vitro. *Curr Opin Nephrol Hypertens* 2, 541-551 (1993).
14. Diaz, R., El-Hajj Fuleihan, G. & Brown, E. M. in Handbook of Physiology, Section 7: Endocrinology, Vol. 3. (ed. G. G. S. Fray) (Oxford University Press, New York; 1999).
15. Madore, G. R., Sherman, P. J. & Lane, J. M. Parathyroid hormone. *J Am Acad Orthop Surg* 12, 67-71 (2004).
16. Potts, J. T. & Juppner, H. in Principles of Bone Biology. (eds. J. P. Bilezikian, L. G. Raisz & G. A. Rodan) 325 (Academic Press, New York; 1996).
17. Qian, J. et al. Midgestational lethality in mice lacking the parathyroid hormone (PTH)/PTH-related peptide receptor is associated with abrupt cardiomyocyte death. *Endocrinology* 144, 1053-1061 (2003).
18. Tian, J., Smogorzewski, M., Kedes, L. & Massry, S. G. Parathyroid hormone-parathyroid hormone related protein receptor messenger RNA is present in many tissues besides the kidney. *Am J Nephrol* 13, 210-213 (1993).
19. Calvi, L. M. et al. Osteoblastic cells regulate the haematopoietic stem cell niche. *Nature* 425, 841-846 (2003).
20. Marie, P. J. Role of N-cadherin in bone formation. *J Cell Physiol* 190, 297-305 (2002).
21. Reya, T. et al. A role for Wnt signalling in self-renewal of haematopoietic stem cells. *Nature* 423, 409-414 (2003).
22. Zhu, J. & Emerson, S. G. A new bone to pick: osteoblasts and the haematopoietic stem-cell niche. *Bioessays* 26, 595-599 (2004).
23. Duarte, R. F. & Frank, D. A. SCF and G-CSF lead to the synergistic induction of proliferation and gene expression through complementary signaling pathways. *Blood* 96, 3422-3430 (2000).
24. Duarte, R. F. & Frank, D. A. The synergy between stem cell factor (SCF) and granulocyte colony-stimulating factor (G-CSF): molecular basis and clinical relevance. *Leuk Lymphoma* 43, 1179-1187 (2002).
25. Hematti, P. et al. Comparison of retroviral transduction efficiency in CD34+ cells derived from bone marrow versus G-CSF-mobilized or G-CSF plus stem cell factor-mobilized peripheral blood in nonhuman primates. *Stem Cells* 22, 1062-1069 (2004).
26. Hess, D. A. et al. Functional analysis of human hematopoietic repopulating cells mobilized with granulocyte colony-stimulating factor alone versus granulocyte colony-stimulating factor in combination with stem cell factor. *Blood* 100, 869-878 (2002).
27. Taichman, R. S. & Emerson, S. G. Human osteoblasts support hematopoiesis through the production of granulocyte colony-stimulating factor. *J Exp Med* 179, 1677-1682 (1994).

28. Taichman, R. S., Reilly, M. J. & Emerson, S. G. Human osteoblasts support human hematopoietic progenitor cells in vitro bone marrow cultures. *Blood* 87, 518-524 (1996).
29. Taichman, R., Reilly, M., Verma, R., Ehrenman, K. & Emerson, S. Hepatocyte growth factor is secreted by osteoblasts and cooperatively permits the survival of haematopoietic progenitors. *Br J Haematol* 112, 438-448 (2001).
30. Philbrick W M, Wysolmerski J J, Galbraith S, Holt E, Orloff, J J, Yang K H, Vasavada R C, Weir E C, Braodus A E, and Stewart A F. Defining the roles of parathyroid hormone-related protein in normal physiology. Physiol Rev 76: 127-173, 1996.
31. Roca-Cusachs A, DiPette D J, and Nickols G A. Regional and systemic hemodynamic effects of parathyroid hormone-related protein: preservation of cardiac function and coronary and renal flow with reduced
32. Jansen, Johanna, Petra Gres, Christian Umschlag, Frank R. Heinzel, Heike Degenhardt, Klaus-Dieter Schlüter, Gerd Heusch, and Rainer Schulz. Parathyroid hormone-related peptide improves contractile function of stunned myocardium in rats and pigs. Am J Physiol Heart Circ Physiol 284: H49-H55, 2003.
33. Urena P, Kong X F, Abou-Samra A B, Juppner H, Kronenberg H M, Potts J T & Segre G V. PTH/PTHrP receptor messenger ribonucleic acids are widely distributed in rat tissues. Endocrinology 1993; 133:617-623.
34. Calvi L M, Adams G B, Weibrecht K W, Weber J M, Olson D P, et al. 2003. Osteoblastic cells regulate the haematopoietic stem cell niche. Nature 425:841-846.
35. Jung Y, Wang J, Schneider A, Sun Y X, Koh-Paige A J, Osman N I, McCauley, Taichmann R S. Regulation of SDF-1 (CXCL12) production by osteoblasts; a possible mechanism for stem cell homing. Bone 2005:
36. Orlic, D., Kajstura, J., Chimenti, S., Jakoniuk, I., Anderson, S. M., Li, B., Pickel, J., McKay, R., Nadal-Ginard, B., Bodine, D. M., Leri, A., and Anversa, P. (2001) Bone marrow cells regenerate infarcted myocardium. *Nature* 410, 701-705
37. Kocher, A. A., Schuster, M. D., Szabolcs, M. J., Takuma, S., Burkhoff, D., Wang, J., Homma, S., Edwards, N. M., and Itescu, S. (2001) Neovascularization of ischemic myocardium by human bone-marrow-derived angioblasts prevents cardiomyocyte apoptosis, reduces remodeling and improves cardiac function. Nat Med 7, 430-436
38. Strauer, B. E., Brehm, M., Zeus, T., Koestering, M., Hernandez, A., Sorg, R. V., Koegler, G., and Wernet, P. (2002) Repair of infarcted myocardium by autologous intracoronary mononuclear bone marrow cell transplantation in humans. Circulation 106, 1913-1918
39. Stamm, C., Westphal, B., Kleine, H. D., Petzsch, M., Kittner, C., Klinge, H., Schumichen, C., Nienaber, C. A., Freund, M., and Steinhoff, G. (2003) Autologous bone-marrow stem-cell transplantation for myocardial regeneration. Lancet 361, 45-46
40. Assmus, B., Schaechinger, V., Teupe, C., Britten, M., Lehmann, R., Doebert, N., Gruenwald, F., Aicher, A., Urbich, C., Martin, H., Hoelzer, D., Dimmeler, S., and Zeiher, A. M. (2002) Transplantation of progenitor cells and regeneration enhancement in acute myocardial infarction. Circulation 106, 3009-3017
41. Orlic, D., Kajstura, J., Chimenti, S., Limana, F., Jakoniuk, I., Quaini, F., Nadal-Ginard, B., Bodine, D. M., Leri, A., and Anversa, P. (2001) Mobilized bone marrow cells repair the infarcted heart, improving function and survival. Proc Natl Acad Sci USA 98, 10344-10349
42. Ohtsuka, M., Takano, H., Zou, Y., Toko, H., Akazawa, H., Qin, Y., Suzuki, M., Hasegawa, H., Nakaya, H., and Komuro, I. (2004) Cytokine therapy prevents left ventricular remodeling and dysfunction after myocardial infarction through neovascularization. FASEB J, Epub ahead of print
43. Kuethe, F., Figulla, H. R., Voth, M., Richartz, B. M., Opfermann, T., Sayer, H. G., Krack, A., Fritzenwanger, M., Hoffken, K., Gottschild, D., and Werner, G. S. (2004) Mobilization of stem cells by granulocyte colony-stimulating factor for the regeneration of myocardial tissue after myocardial infarction. Dtsch Med Wochenschr 129, 424-428
44. Yang, F., Liu, Y. H., Yang, X. P., Xu, J., Kapke, A., and Carretero, O. A. (2002) Myocardial infarction and cardiac remodelling in mice. Exp Physiol 87, 547-555
45. Wettschureck, N., Ruetten, H., Zywietz, A., Gehring, D., Wilkie, T. M., Chen, J., Chien, K. R., and Offermenns, S. (2001) Absence of pressure overload induced myocardial hypertrophy after conditional inactivation of Gaq/Ga11 in cardiomyocytes. Nat Med 7, 1236-1240
46. Georgakopoulos, D., Mitzner, W. A., Chen, C. H., Byrne, B. J., Millar, H. D., Hare, J. M., and Kass, D. A. (1998) In vivo murine left ventricular pressure-volume relations by miniaturized conductance micromanometry. Am J Physiol 274, H1416-1422
47. Tanaka, J., Miyake, T., Shimizu, T., Wakajana, T., Tsumori, M., Koshimura, K., Murakami, Y., and Kato, Y. (2002) Effect of continuous subcutaneous administration of a low dose of G-CSF on stem cell mobilization in healthy donors: a feasibility study. Int J Hematol 75, 489-492
48. Kawashima-Ohaya Y, Satakeda H, Kuruta Y, Kawamoto T, Yan W, Akagawa Y, Hayakawa T, Noshiro M, Okada Y, Nakamura S and Kato Y. Effects of Parathyroid Hormone (PTH) and PTH-Related Peptide on Expressions of Matrix Metalloproteinase-2, -3, and -9 in Growth Plate Chondrocyte Cultures. *Endocrinology* 139: 2120-2127, 1998.
49. McClelland P, Onyia J E, Miles R R, Tu Y, Liang J, Harvey A K, Chandrasekhar S, Hock J M, Bidwell JP. Intermittent administration of parathyroid hormone (1-34) stimulates matrix metalloproteinase-9 (MMP-9) expression in rat long bone. J Cell Biochem. 1998 Sep. 1; 70(3):391-401.
50. Feola M, Gonzales H, Canizaro PC. Vasoactive parathyroid hormone in the treatment of acute ischemic left ventricular failure and the prevention of cardiogenic shock. Circ Shock. 1985; 17(2): 163-77.
51. Palmen M, Daemen M J, Bronsaer R, Dassen W R, Zandbergen H R, Kockx M, Smits J F, van der Zee R, Doevendans P A. Cardiac remodeling after myocardial infarction is impaired in IGF-1 deficient mice. Cardiovasc Res. June; 50(3):516-24.
52. Balsam, L. B., Wagers, A. J., Christensen, J. L., Kofidis, T., Weissman, I. L., and Robbins, R. C. (2004) Haematopoietic stem cells adopt mature haematopoietic fates in ischaemic myocardium. Nature. 428, 668-673
53. Murry, C. E., Soonpaa, M. H., Reinecke, H., Nakajima, H., Nakajima, H. O., Rubart, M., Pasumarthi, K. B., Virag, J. I., Bartelmez, S. H., Poppa, V., Bradford, G., Dowell, J. D., Williams, D. A., and Field, L. J. (2004) Haematopoietic stem cells do not transdifferentiate into cardiac myocytes in myocardial infarcts. Nature 428, 664-668
54. Harada, M., Qin, Y., Takano, H., Minamino, T., Zou, Y., Toko, H., Ohtsuka, M., Matsuura, K., Sano, M., Nishi, J., wanaga, K., Akazawa, H., Kunieda, T., Zhu, W., Hasegawa, H., Kunisada, K., Nagai, T., Nakaya, H., Yamauchi-Takihara, K., and Komuro, I. (2005) G-CSF prevents cardiac remodeling after myocardial infarction by activating the Jak-Stat pathway in cardiomyocytes. Nat Med 11, 305-311

55. Fuste, B., Mazzara, R., Escolar, G., Merino, A., Ordinas, A., and Diaz-Ricart, M. (2004) Granulocyte colony-stimulating factor increases expression of adhesion receptors on endothelial cells through activation of p38 MAPK. Haematologica 89, 578-585
56. Bussolino, F., Wang, J. M., Defilippi, P., Turrini, F., Sanavio, F., Edgell, C. J., Aglietta, M., Arese, P., and Mantovani, A. (1989) Granulocyte- and granulocyte-macrophage-colony stimulating factors induce human endothelial cells to migrate and proliferate. Nature 337, 471-473
57. Hoefer, I. E., Grundmann, S., van Royen, N., Voskuil, M., Schirmer, S. H., Ulusans, S., Bode, C., Buschmann, I. R., and Piek, J. J. (2005) Leukocyte subpopulations and arteriogenesis: Specific role of monocytes, lymphocytes and granulocytes. 181, 285-289
58. Heil, M., Ziegelhoeffer, T., Pipp, F., Kostin, S., Martin, S., Clauss, M., and Schaper, W. (2002) Blood monocyte concentration is critical for enhancement of collateral artery growth. Am J Physiol Heart Circ Physiol 283, H2411-2419
59. Hoefer, I. E., van Royen, N., Rectenwald, J. E., Deindl, E., Hua, J., Jost, M., Grundmann, S., Voskuil, M., Ozaki, C. K., Piek, J. J., and Buschmann, I. R. (2004) Arteriogenesis proceeds via ICAM-1/Mac-1-mediated mechanisms. Circ Res Epub ahead of print
60. Deindl, E., Ziegelhoffer, T., Kanse, S. M., Fernandez, B., Neubauer, E., Carmeliet, P., Preissner, K. T., and Schaper, W. (2003) Receptor-independent role of the urokinase-type plasminogen activator during arteriogenesis. FASEB J, 1174-1176
61. Ziegelhoeffer, T., Fernandez, B., Kostin, S., Heil, M., Voswinckel, R., Helisch, A., and Schaper, W. (2003) Bone Marrow-Derived Cells Do Not Incorporate Into the Adult Growing Vasculature. Circ Res 94, Epub ahead of print
62. Norol, F., Merlet, P., Isnard, R., Sebillon, P., Bonnet, N., Cailliot, C., Carrion, C., Ribeiro, M., Charlotte, F., Pradeau, P., Mayol, J. F., Peinnequin, A., Drouet, M., Safsafi, K., Vernant, J. P., and Herodin, F. (2003) Influence of mobilized stem cells on myocardial infarct repair in a non-human primate model. Blood 102, 4361-4368
63. Deten, A., Volz, H. C., Clamors, S., Leiblein, S., Briest, W., Marx, G., and Zimmer, H. G. (2005) Hematopoietic stem cells do not repair the infarcted mouse heart. Cardiovasc Res 65, 52-63
64. Deindl, E., Helisch, A., Scholz, D., Heil, M., Wagner, S., and Schaper, W. (2004) Role of hypoxia/ischemia/VEGF-A and strain differences. In Arteriogenesis (Schaper, W., and Schaper, J., eds) pp. 115-131, Kluwer Academic Publishers, Boston Dordrecht London
65. Kong, D., Melo, L. G., M., G., Zhang, L., Mostoslavsky, G., Liew, C. C., Pratt, R. E., and Dzau, V. J. (2004) Cytokine-induced mobilization of circulating endothelial progenitor cells enhances repair of injured arteries. Circulation
66. Herold, J., Pipp, F., Fernandez, B., Xing, Z., Heil, M., Tillmanns, H., and Braun-Dullaeus, R. C. (2004) Transplantation of monocytes: a novel strategy for in vivo augmentation of collateral vessel growth. Hum Gene Ther 15, 1-12
67. Schneeloch, E., Mies, G., Busch, H. J., Buschmann, I. R., and Hossmann, K. A. (2004) Granulocyte-macrophage colony-stimulating factor-induced arteriogenesis reduces energy failure in hemodynamic stroke. Proc Natl Acad Sci USA 101, 12730-12735
68. Buschmann, I. R., Hoefer, I. E., van Royen, N., Katzer, E., Braun-Dullaeus, R., Heil, M., Kostin, S., Bode, C., and Schaper, W. (2001) GM-CSF: a strong arteriogenic factor acting by amplification of monocyte function. Atherosclerosis 159
69. Buschmann, I. R., Busch, H. J., Mies, G., and Hossmann, K. A. (2003) Therapeutic induction of arteriogenesis in hypoperfused rat brain via granulocyte-macrophage colony-stimulating factor. Circulation 108, 610-615
70. Seiler, C., Pohl, T., Wustmann, K., Hutter, D., Nicolet, P. A., Windecker, S., Eberli, F. R., and Meier, B. (2001) Promotion of collateral growth by granulocyte-macrophage colony-stimulating factor in patients with coronary artery disease: a randomized, double-blind, placebo-controlled study. Circulation 23, 2012-2017
71. Sugano, Y., Anzai, T., Yoshikawa, T., Maekawa, Y., Kohno, T., Mahara, K., Naito, K., and Ogawa, S. (2005) Granulocyte colony-stimulating factor attenuates early ventricular expansion after experimental myocardial infarction. Cardiovasc Res 65, 446-456
72. Peter, F. W., Schuschke, D. A., Barker, J. H., Fleishcher-Peter, B., Pierangeli, S., Vogt, P. M., and Steinau, H. U. (1999) The effect of severe burn injury on proinflammatory cytokines and leukocyte behavior: its modulation with granulocyte colony stimulating factor. Burns 25, 477-486
73. Vargel, I., Erdem, A., Ertoy, D., Pinar, A., Erk, Y., Altundag, M. K., and Gullu, I. (2002) Effects of growth factors on doxorubicin-induced skin necrosis: documentation of histomorphological alterations and early treatment by GM-CSF and G-CSF. Ann Plastic Surg 49, 646-653
74. Carstanjen, D., Ulbricht, N., Iacone, A., Regenfus, M., and Salama, A. (2002) Matrix metalloproteinase-9 (gelatinase B) is elevated during mobilization of peripheral blood progenitor cells by G-CSF. Transfusion 42, 588-596
75. Minatugucchi, S., Takemura, G., Chen, X. H., Wang, N., Uno, Y., Koda, M., Arai, M., Misao, Y., Lu, C., Suzuki, K., Goto, K., Komada, A., Takahashi, T., Kosai, K., Fujiwara, T., and Fujiwara, H. (2004) Acceleration of the healing process and myocardial regeneration may be important as a mechanism of improvement of cardiac function and remodeling by postinfarction Granulocyte Colony-Stimulating Factor treatment. Circulation 109, 2572-2580

Figure 5:
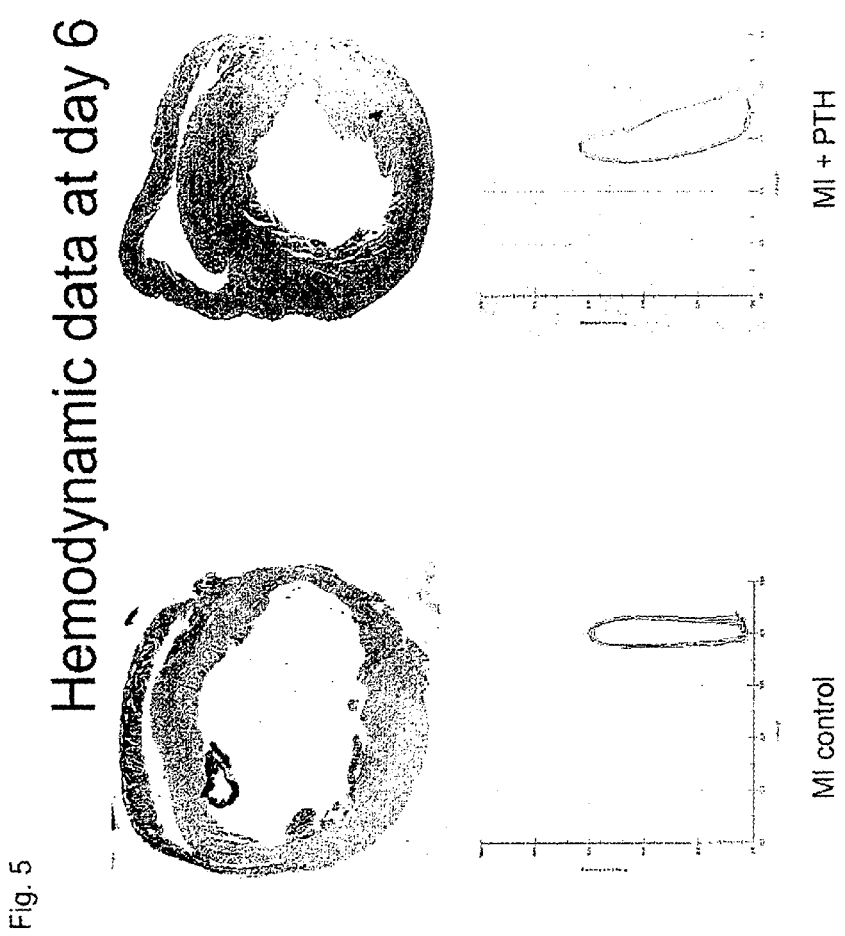

The Figures show:

FIG. 1: A CD45$^+$/CD34$^+$ cell populations in peripheral blood (relative values)
B CD45$^+$/CD34$^-$ cell populations in peripheral blood (relative values)
* significant compared to control
** significant compared to PTH 6d
*** significant compared to PTH 14d
FIG. 2: A CD45$^+$/CD34$^+$ cell populations in bone marrow
* B CD45$^+$/CD34$^-$ cell populations in bone marrow
** significant compared to control
*** significant compared to PTH 6d
significant compared to PTH 14d
FIG. 3: A Serum levels of SCF
B Serum levels of G-CSF
* significant compared to control
FIG. 4: Mortality amongst mice treated with PTH and with saline in which myocardial infarction has been induced
4 weeks after myocardial infarction, rPTH (1-34) treated mice showed a significant increase in the survival rate compared to saline treated animals (60.0% vs. 40.2%). Mortality amongst untreated mice was very high within the first six days.
FIG. 5: Hemodynamic data at day 6
Using conductance catheters pressure volume relations were measured from baseline (sham and control animals), PTH (1-34) treated as well as saline treated mice at day 6 after the surgically induced myocardial infarction in vivo.

Figure 6:
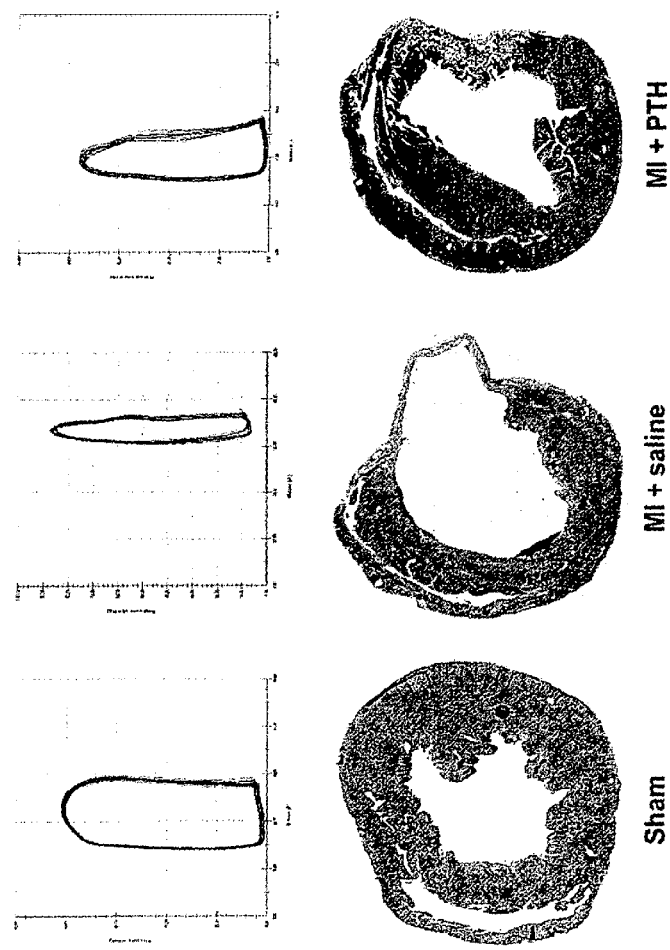

FIG. 6: Hemodynamic data at day 30

Using conductance catheters pressure volume relations were measured from baseline (sham and control animals), PTH (1-34) treated as well as saline treated mice at day 30 after the surgically induced myocardial infarction in vivo.

Figure 7:
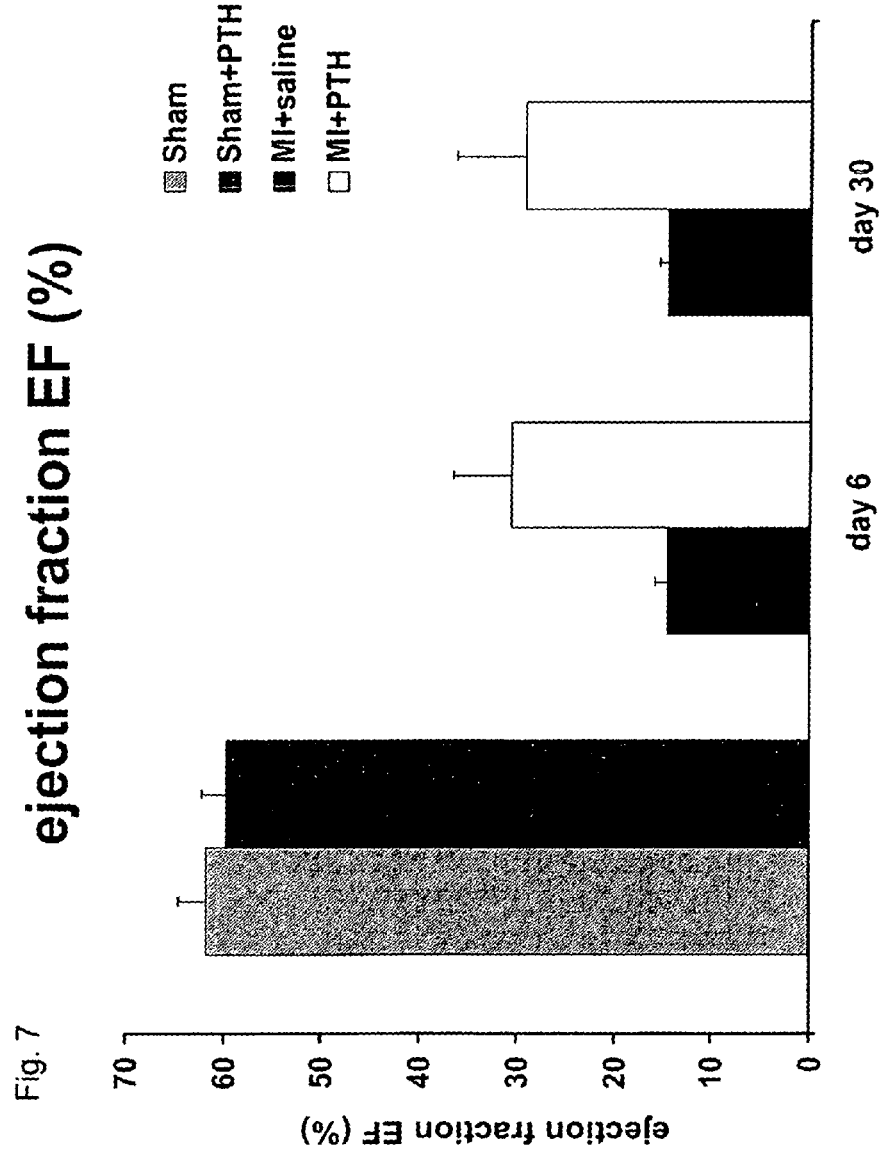

FIG. 7: Ejection Fraction

At day 6 PTH treatment resulted in an improved systolic function reflected by an increased ejection fraction (30 vs. 15%).

At day 30, hemodynamical improvement was still present in the PTH treated group: Ejection fraction (EF: 29.0±7.1% vs. 14.5±0.9%, p<0.001) was significantly improved.

Figure 8:
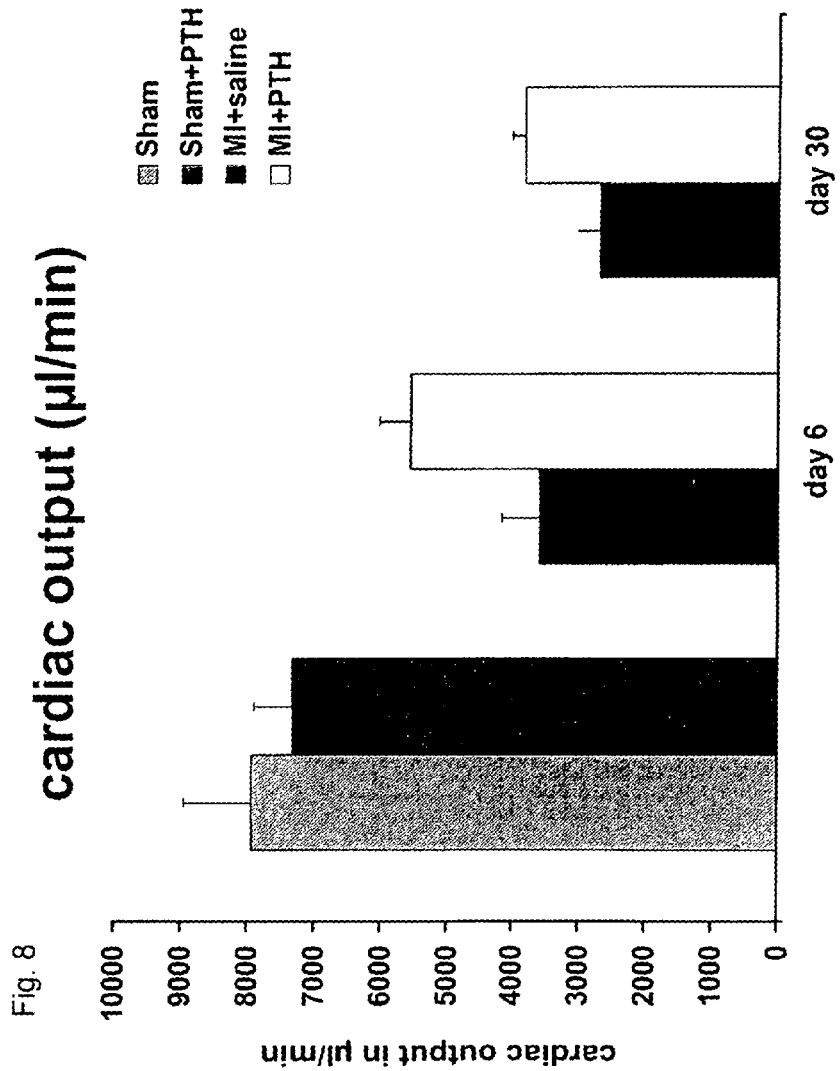

FIG. 8: Cardiac Output

At day 6 PTH treatment resulted in an improved systolic function reflected by an increased cardiac output (5537 vs. 3588 μl/min).

At day 30, hemodynamical improvement was still present in the PTH treated group: cardiac output (3810±205 vs. 2690±329) was significantly improved.

Figure 9:
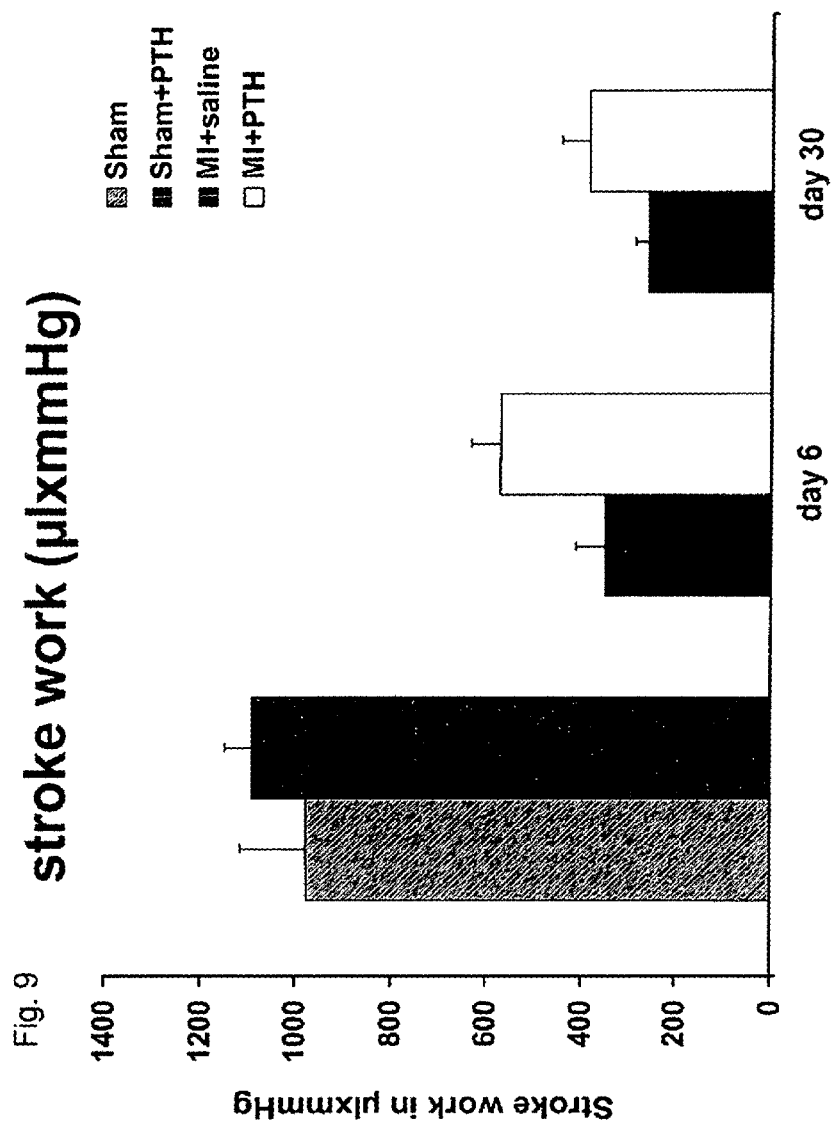

FIG. 9: Stroke work

At day 6 PTH treatment resulted in an improved systolic function reflected by an increased stroke work.

At day 30, hemodynamical improvement was still present in the PTH treated group: stroke work (382±59 vs. 258±27 mmHg×μl, p<0.05).

Figure 10:
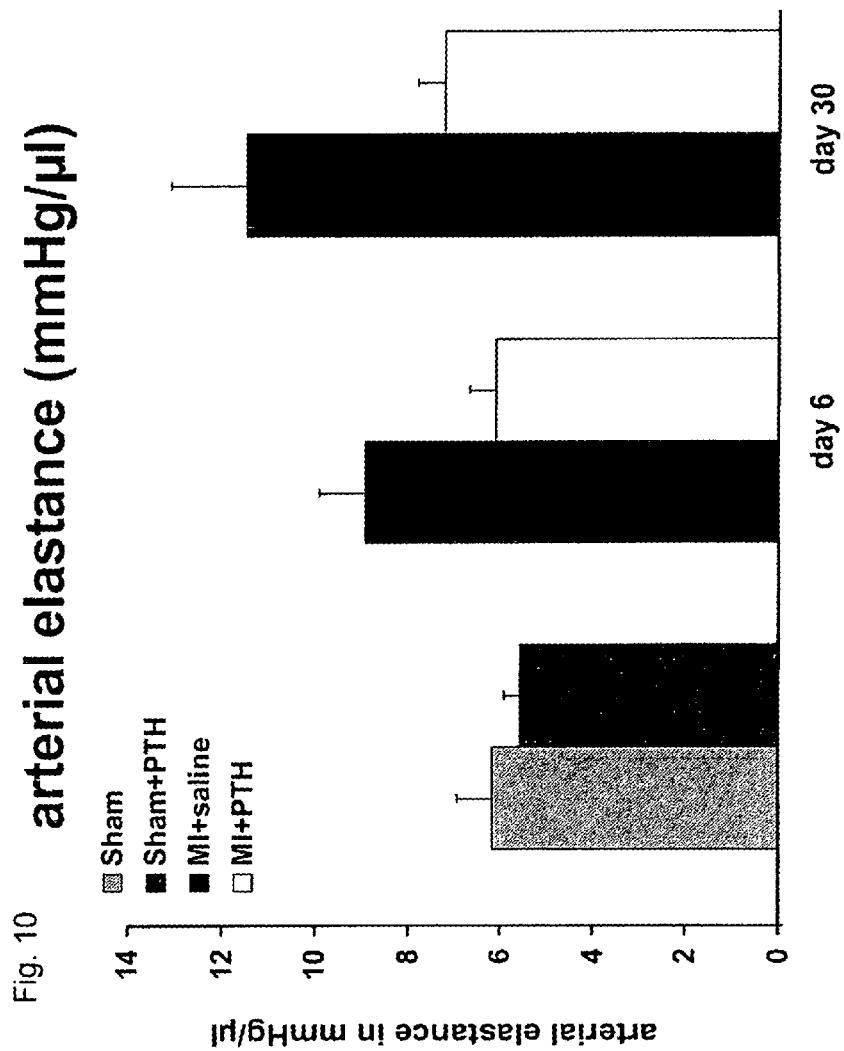

FIG. 10: Arterial elastance

Arterial vascular load was significantly reduced in PTH treated animals reflected by a decreased arterial elastance (Ea: 6.1±0.5 vs. 8.9±0.9 mmHg/μl, FIG. 10). Similar to the 6 days group arterial elastance (Ea: 7.2±0.5 vs. 11.5±1.6 mmHg/μl) was significantly reduced 30 days after hormone treatment.

Figure 11:
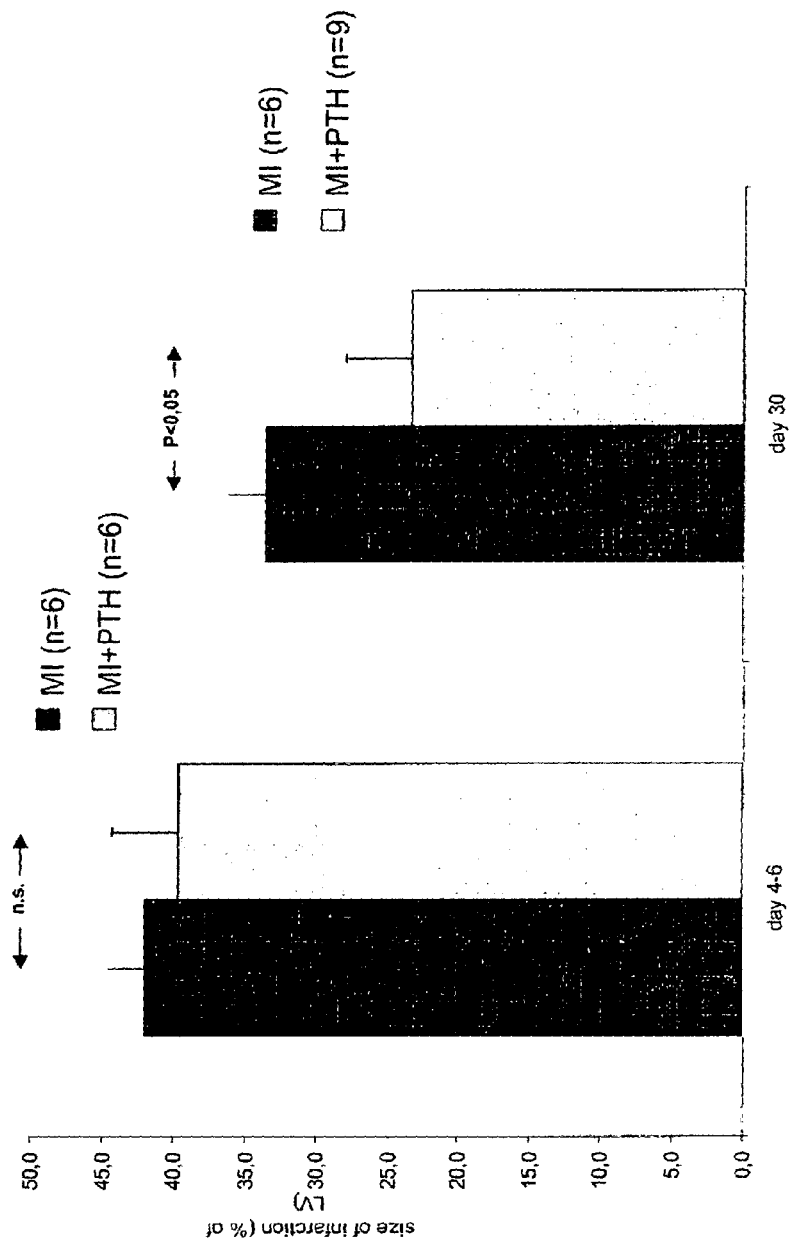

FIG. 11: Size of infarction

At day 30, saline treated infarcted mice revealed a transmural myocardial infarction with pronounced wall thinning over time and apical aneurysms in, whereas rPTH (1-34) treatment was associated with a lower frequency of large LV-aneurysms (see FIG. 6). LV-infarct size at day 6 calculated as area of necrosis and granulation tissue (37.3±4.9% vs. 39.8±3.1% of total LV area, p=ns) was not significantly different compared to saline treatment.

Figure 12:
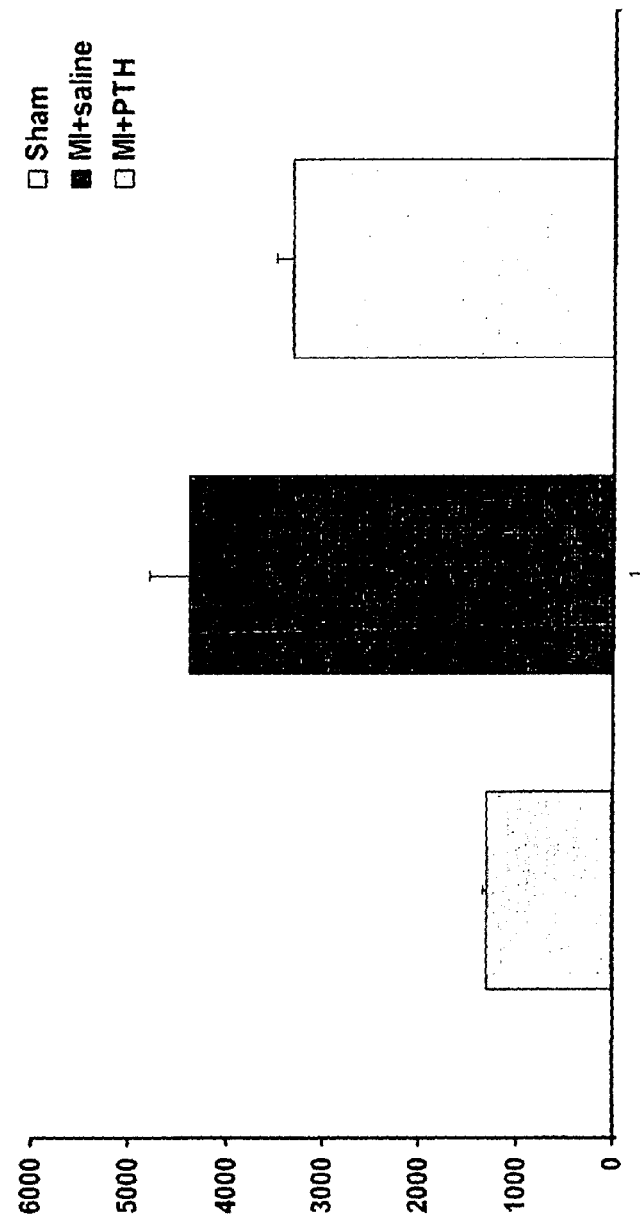

FIG. 12: Number of cells in the area of infarction

At day 30, saline treated infarcted mice revealed a transmural myocardial infarction with pronounced wall thinning over time and apical aneurysms in, whereas rPTH (1-34) treatment was associated with a lower frequency of large LV-aneurysms (FIG. 6). LV-infarct size at day 6 calculated as area of necrosis and granulation tissue (37.3±4.9% vs. 39.8±3.1% of total LV area, p=ns, FIG. 11) was not significantly different compared to saline treatment. However, infarct composition was altered with a significantly lower cellular density (4383±409 vs. 3317±171/mm$^2$, p<0.05) in the granulation tissue.

Figure 13:
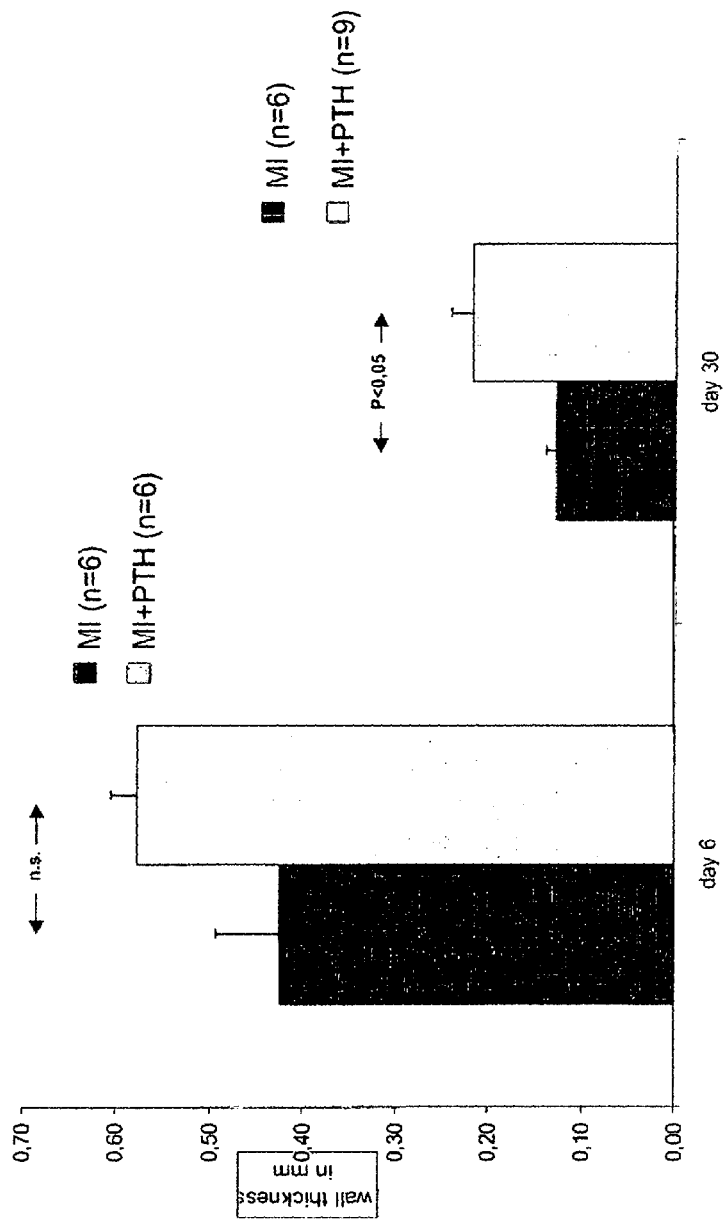

FIG. 13: Wall thickness

At day 30 after LAD occlusion infarct size measured as area of fibrosis was significantly smaller in PTH treated animals (23.3±4.6% vs. 33.6±2.6%, p<0.05, FIG. 11). The anterior wall thickness declined over time in both groups, however, to a smaller extent in G-CSF treated mice (FIG. 6). At day 6 and at day 30 the anterior wall in the group of rPTH treaded animals was thicker compared to saline treated mice (day 6: 0.58 vs. 0.42 mm, day 30: 0.22 vs. 0.13 mm).

Figure 14:
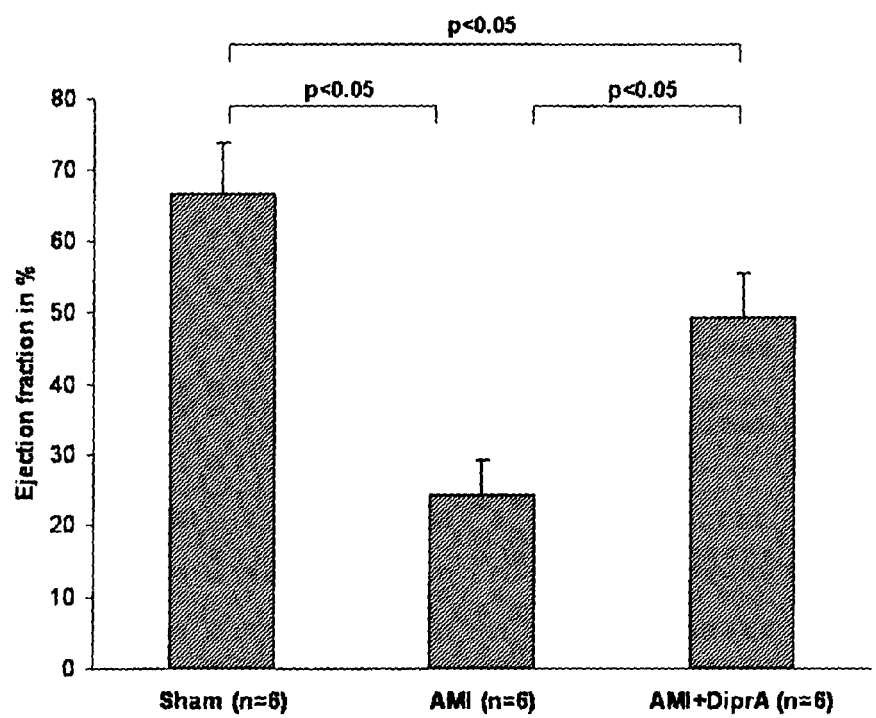

FIG. 14: Improvement of cardiac function after myocardial infarction by increased migration and homing of stem cells to the myocardium via DPP IV inhibition Reduced cardiac function (assessed by Millar-Tip-Katheter) in a mouse modell 6 days after myocardial infarction ("AMI") in comparison to a control group ("sham"). Ejection fraction (EF) improved significantly after DPP-IV-inhibition via diprotin A ("AMI+DiprA") after myocardial infarction.

FIG. 15: Histological findings and pressure volume relations in mice

A. Representative Masson Trichrom staining of infarcted or sham operated hearts (top) in relation to in vivo measured pressure volume relations (bottom) of the same mice 30 days after MI. (Left) sham operated mice, (middle) infarcted and saline treated mice and (right) PTH treated infarcted mice. Sham operated mice revealed normal pressure volume relations with low endsystolic and enddiastolic volumes (left), whereas infarcted animals revealed low LV pressures with high filling volumes resulting in a lower ejection fraction (middle), which was partially restored in G-CSF treated animals resulting in a shift to the left of the PV loops (right).

B. Bar graphs representing the ejection fraction (left) and the arterial elastance (right) of sham operated (n=10, white bars), sham+PTH (n=8, dotted bars), saline treated infarcted (striped bars) and PTH treated infarcted animals (black bars) at 6 days (n=6) and 30 days (n=6-10) after myocardial infarction. *p<0.05 saline vs. PTH.

Figure 16:
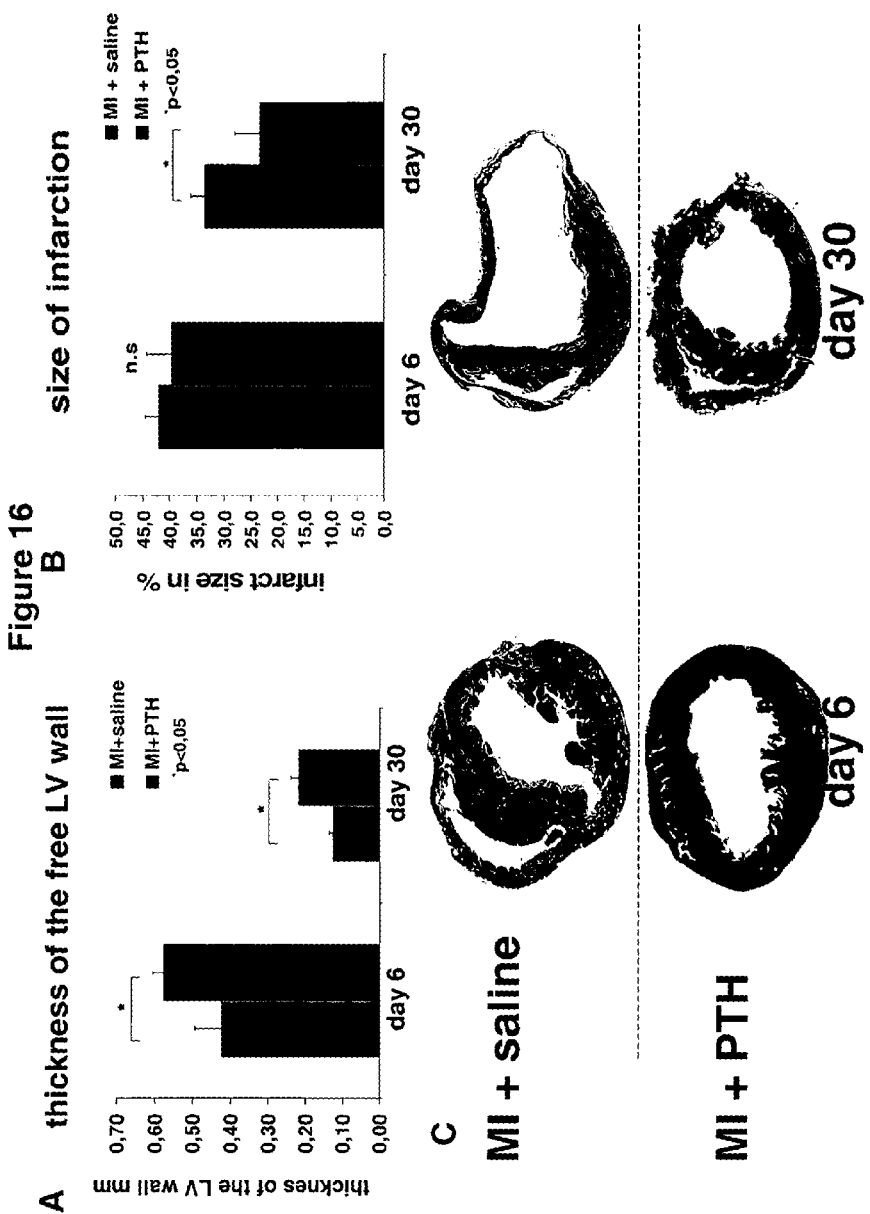

FIG. 16: Infarct size and anterior wall thickness

Bar graphs representing A) the decline of the left anterior free wall and B) the infarct size in saline treated infarcted animals (striped bars) and PTH treated infarcted animals (black bars) at day 6 (n=6) and day 30 (n=6-10) after MI. C) Representative Massons Trichrome stainings of saline treated (top) and PTH treated mice (bottom) at day 6 (left) and day 30 (right) after MI. *p<0.05 saline vs. PTH.

FIG. 17: PTH increased neovascularization in the granulation tissue

A) Bar graphs representing the number of CD31 positive vessels in the granulation tissue at borderzone of saline treated animals (striped bars) and of PTH treated animals (black bars) at day 6 (n=6) and day 30 (n=6) after ligation of the LAD.

B) Representative immunohistochemical staining of CD31 (brown) in the heart of saline treated (left) and PTH treated mice (right) at day 6 (upper row 400×) and day 30 after MI (lower row 400×). C) Representative staining of CD31 positive vessels (left: 100×, right: 400×) in the granulation tissue harboring the borderzone of PTH treated (upper row) and saline treated animals (lower row). D) immunohistochemical analyses of capillaries of PTH treated mice 6 days after MI revealed double staining of CD31 (brown) and Ki67 (violet) positive vessels. All sections nuclei (blue) were counterstained with hematoxyline. *p<0.05 saline vs. PTH.

Figure 18:
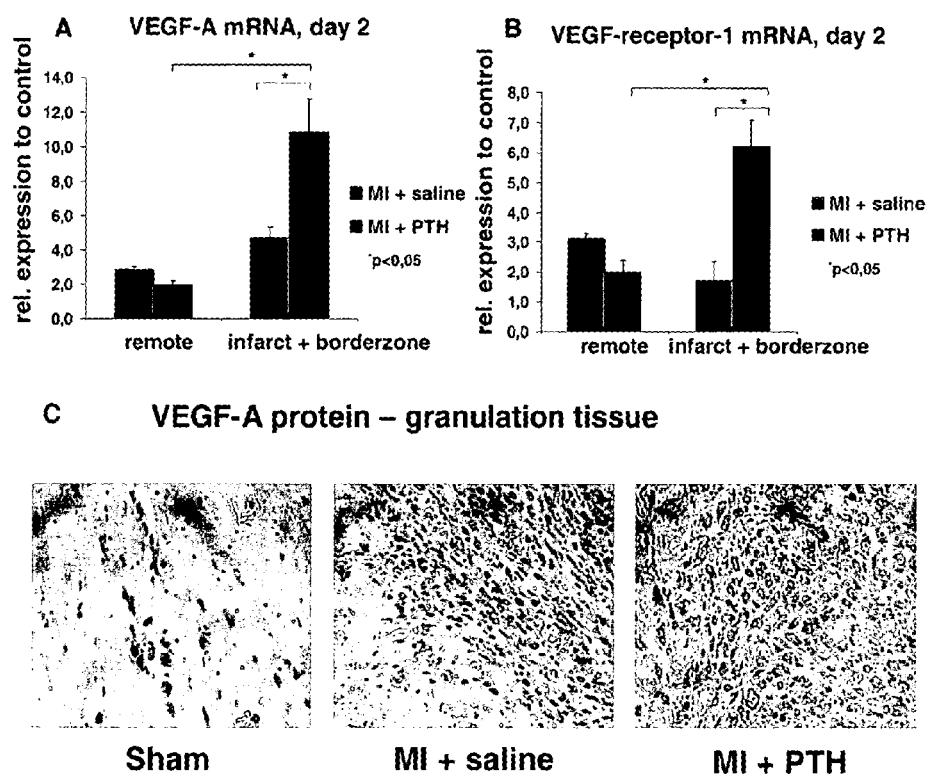

FIG. 18: Immunohistochemical staining of VEGF-A protein in the granulation tissue at the infarct border zone and RT-PCR analysis of VEGF-A/VEGF-R1 expression Bar graphs representing the relative fold increase of VEGF-A (left, 18A) and VEGF-1 receptor (right, 18B) mRNA expression of saline treated (n=3, striped bars) and of PTH treated myocardial tissue (n=3-5, black bars) normalized to non infarcted control mice (n=3) 48 hours after myocardial infarction, *p<0.05.

C) Representative staining of VEGF-A protein (brown) in the granulation tissue of sham operated (left), saline (middle) and PTH treated hearts (right). VEGF-A protein is mainly localized on infiltrated cells in the granulation tissue at the border zone.

Figure 19:
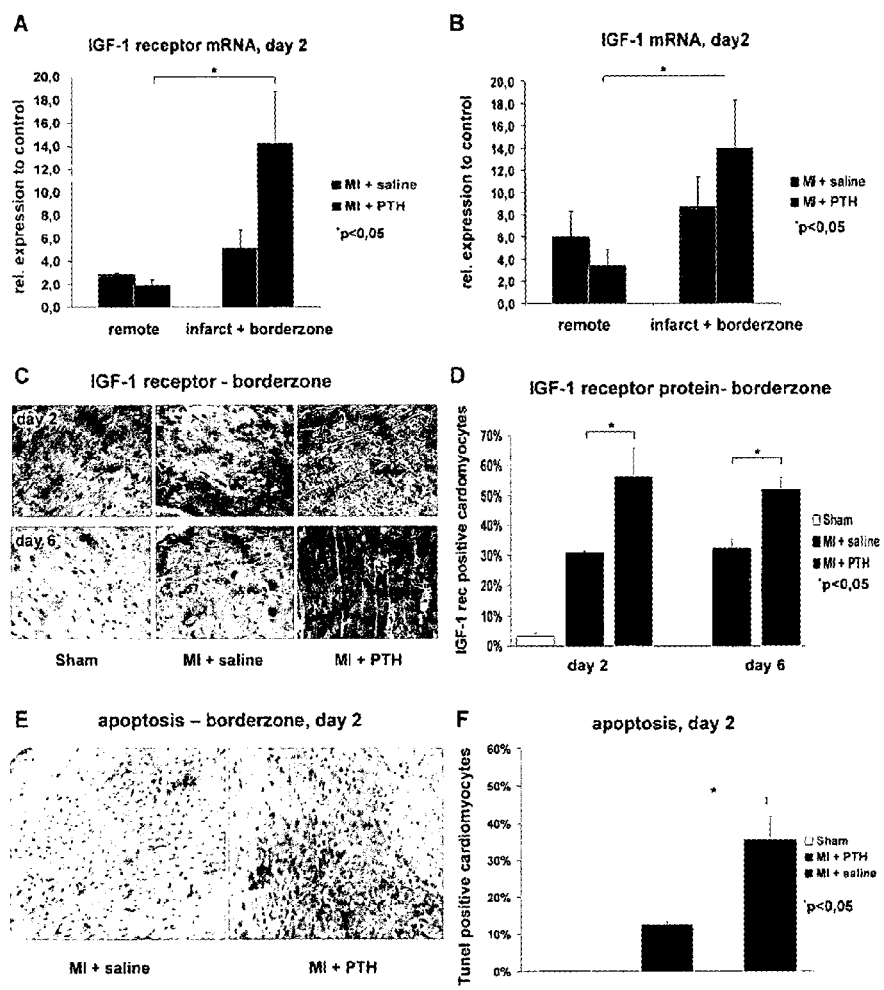

FIG. 19: Expression patterns of IGF-1/IGF-1 and its influence on apoptosis

A) Bar graphs representing the relative fold increase of IGF-1 receptor and B) IGF-1 mRNA expression of saline treated (n=3, striped bars) and PTH treated mice (n=3-5, black bars) normalized to non infarcted control mice (n=3) 48 hours after myocardial infarction. *p<0.05. C) Immunohistochemical staining of IGF-1 receptor protein (brown) positive cardiomyocytes in the borderzone of sham operated (n=3, left), saline treated (n=3, middle) and PTH treated animals (n=5, right) at 2 days (upper row) und 6 days (lower row) after MI. D) Bar graph representing the percentage of IGF-1 receptor positive cardiomyocytes in the borderzone. E-F) Tunel staining and quantification of Tunel positive cardiomyocytes in the infarct borderzone 48 hours after MI of sham operated (n=3, white bars), saline treated (n=3, striped bars) and of PTH treated animals (n=3-5, black bars). *p<0.05.

FIG. 20: FIGS. 20A-C Shows PTH Induced Migration of $CD45^+$ Stem Cells.

FIG. 20A shows PTH-induced migration of $CD45^+/CD34^+/CXCR4^+$ cells and $CD45^+/Sca-1^+/CXCR-4^+$ cells. FIG. 20B shows the cell migration of $CD45^+$ cells to the ischemic heart. FIG. 20C shows the percent stem cell markers on $CD45^+/CD34^+$ cells.

FIG. 21: FIGS. 21A-C PTH induced migration of $CD45^+$ stem cells.

FIG. 21A shows PTH-induced migration of stem cells. FIG. 21B shows the migration of $CD45+/CD34^+$ cells to the ischemic heart in controls, in saline treated and PTH treated animals after myocardial infarction (MI). FIG. 21C shows SDF-1 mRNA increase in myocardial infarction animals (MI), saline treated versus PTH treated.

The following Examples illustrate the present invention. These Examples should not be construed as to limit the scope of this invention. The Examples are included for purposes of illustration and the present invention is limited only by the claims.

FIRST SET OF EXPERIMENTS

Stem Cell Mobilization

EXAMPLE 1

Animals

For the experiments healthy age- and sex-matched (male, 8-12 weeks of age) C57BL/6 mice (Charles River) were used. Animal care and all experimental procedures were performed in strict accordance to the German and National Institutes of Health animal legislation guidelines and were approved by the local animal care and use committees.

EXAMPLE 2

Administration of PTH or G-CSF

Mice were divided into the following groups: 1) administration of saline daily for 6 days, sacrificed at day 7 (n=6). 2) administration of PTH (Bachem) daily for 6 consecutive days (80 µg per kg body weight per day, intraperitoneally), sacrificed at day 7 (n=6). 3) administration of PTH daily for 14 consecutive days, sacrificed at day 15 (n=6). 4) administration of G-CSF (Amgen Biologicals) daily for 5 consecutive days (200 µg per kg body weight per day, intraperitoneally), sacrificed at day 6 (n=6).

EXAMPLE 3

Flow Cytometry Analysis

At day 6, 1 ml of peripheral blood was harvested from each mouse by aspirating the carotid artery. Bone marrow cells were obtained by flushing the tibias and femurs from the euthanized mice. Mononuclear cells were separated by density-gradient centrifugation using 1.077 g/mL Histopaque solution (Sigma Chemicals), purified and resuspended in phosphate-buffered saline (PBS) containing 1% bovine serum albumin. Cells were incubated for 40 minutes in the dark at 4° C. with following fluorescein-isothiocyanate (FITC), phycoerythrin (PE), and peridinin-chlorphyll-protein (PerCP) conjugated monoclonal antibodies: CD45-PerCP, C34-FITC, CD31-PE, Sca-1-PE and c-kit-PE (all from BD Pharmingen). Isotype-identical antibodies (BD Pharmingen) served as controls. Cells were analyzed by 3-color flow cytometry using a Coulter® Epics® XL-MCL™ flow cytometer (Beckman Coulter). Each analysis included 20000 events. The absolute number of antigen-positive cells per ml of whole blood was calculated by multiplying the percentage of antigen-positive cells with the total number of mononuclear cells per ml of blood detected by the conventional hematological cell analyzer. The number of lymphocytes together with the number of monocytes comprised the total number of mononuclear cells.

EXAMPLE 4

G-CSF and SCF Serum Levels

G-CSF and SCF serum levels were determined by ELISA (Mouse G-CSF and Mouse SCF, RayBiotech).

EXAMPLE 5

Statistical Analysis

Data are shown as mean±SEM. Multiple group comparison was performed by one-way analysis of variance (ANOVA) followed by the Bonferroni procedure for comparison of means. Comparisons between two groups were performed using the unpaired t-test. Values of P<0.05 were considered statistically significant.

EXAMPLE 6

$CD45^+/CD34^+$ and $CD45^+/CD34^-$ Cell Populations in Peripheral Blood after PTH Treatment Investigating mononuclear cells via flow cytometry analysis, we found a significant increase of different subtypes of $CD45^+/CD34^+$ cells ($CD45^+/CD34^+/CD31^+$, $CD45^+/CD34^+/Sca-1^+$, $CD45^+/CD34^+/c-kit^+$) and $CD45^+/CD34^-$ cells ($CD45^+/CD34^-/CD31^+$, $CD45^+/CD34^-/Sca-1^+$, $CD45^+/CD34^-/c-kit^+$) in peripheral blood at day 6 and day 14 of PTH stimulation. However, there were no significant differences between 6 and 14 days of treatment (FIG. 1A+B).

EXAMPLE 7

$CD45^+/CD34^+$ and $CD45^+/CD34^-$ Cell Populations in Peripheral Blood after G-CSF Treatment The results showed a significant increase of different subtypes of $CD45^+/CD34^+$ cells and $CD45^+/CD34^-$ cells in peripheral blood at day 6 of G-CSF stimulation (FIG. 1A+B).

Comparing PTH and G-CSF treatment we found a significant lower number of mobilized subtypes of $CD45^+/CD34^+$ cells after PTH administration. No significant changes were detected in mobilized subtypes of $CD45^+/CD34^-$ cells except for $CD45^+/CD34^-/c\text{-}kit^+$ cells (49-50%, p<0.05) (FIG. 1A+B).

EXAMPLE 8

$CD45^+/CD34^+$ and $CD45^+/CD34^-$ Cell Populations in Bone Marrow after PTH Treatment In bone marrow no significant change of subtypes of $CD45^+CD34^+$ cells was detectable at day 6 or day 14 of PTH stimulation (FIG. 2A).

The subtypes of $CD45^+/CD34^-$ cells however, showed a significant decrease at day 6 of PTH stimulation (FIG. 2B).

EXAMPLE 9

$CD45^+/CD34^+$ and $CD45^+/CD34^-$ Cell Populations in Bone Marrow after G-CSF Treatment In contrast to PTH treated animals G-CSF treatment resulted in a significant decrease of all subtypes of $CD45^+ CD34^+$ cells compared to the control group (FIG. 2 A).

$CD45^+/CD34^-$ cells are significantly increased in bone marrow after G-CSF treatment (18.9% increase compared to saline treated mice, p<0.001), whereas all investigated subtypes of $CD45^+/CD34^-$ cells are significantly decreased (FIG. 2B).

EXAMPLE 10

Serum Levels of Cytokines

Serum levels of G-CSF analysed by ELISA were significantly elevated at day 6 of PTH stimulation (2171.0±93.6 µg/ml vs. 6035.5±1318.4 µg/ml, p<0.05). SCF showed significant decreased levels at day 6 of PTH stimulation (670.4±19.1 µg/ml vs. 594.6±26.8 µg/ml, p<0.05). (FIG. 3A+B).

SECOND SET OF EXPERIMENTS

Myocardial Infarction

EXAMPLE 11

Animal Model

Myocardial infarction was induced in male C57BL/6 mice 8-12 weeks of age by surgical occlusion of the left anterior descending artery (LAD) through a left anterolateral approach. Mice were anesthetized by intraperitoneal injection of a mixture of 100 mg/kg ketamine (Sigma Chemical Co., St. Louis, Mo.) and 5 mg/kg Xylazine (Sigma), intubated and artificially ventilated by a mouse ventilator (HUGO SACHS, March, Germany) with 200 strokes/min and 200 µl/stroke. Animal care and all experimental procedures were performed in strict accordance to the German and National Institutes of Health animal legislation guidelines and were approved by the local animal care and use committees.

EXAMPLE 12

Administration of PTH (1-34) and Bromodeoxyuridine (BrdU)

After occlusion of the LAD, mice were divided into the following groups 1) subcutaneous administration of saline daily for 5 days, sacrificed at day 6 (n=10) and day 30 (n=15); 2) administration of rat PTH (1-34) daily for 5 and 14 consecutive days (80 µg/kg/d s.c., Bachem), sacrificed at day 6 (n=9) and day 30 (n=15); 3) sham operated animals sacrificed at day 30 (n=5), and not operated control animals receiving saline (n=6) sacrificed at day 6 and at day 30. All animals received BrdU (50 µg/kg/d) for 5 consecutive days. BrdU and cytokine treatment were started 12-24 hours after LAD occlusion.

EXAMPLE 13

Flow Cytometry Analyses 8-12 week old C57BL/6 mice (n=5) were either treated with PTH (80 µg/kg/d) or saline daily for 5 or 14 consecutive days. At day 6 and day 14, 1 ml of peripheral blood was harvested from each mouse by aspirating the carotid artery. To define the number of leukocytes, heparinized blood samples were analyzed using a conventional hematological cell analyzer (Sysmex XE 2100). Mononuclear cells were separated by density-gradient centrifugation using Histopaque solution (1.077 g/ml, Sigma Chemicals), purified and resuspended in phosphate-buffered saline (PBS) containing 1% bovine serum albumin. Cells were incubated for 40 minutes in the dark at 4° C. with the following fluorescein-isothiocyanate (FITC), phycoerythrin (PE), and peridinin-chlorophyll-protein (PerCP) conjugated monoclonal antibodies: CD45-PerCP, CD34-FITC, CD31-PE, Sca-1-PE and c-kit-PE (all from BD Pharmingen). Matching isotype antibodies (BD Pharmingen) served as controls. Cells were analyzed by 3-color flow cytometry using a Coulter® Epics® XL-MCL™ flow cytometer (Beckman Coulter). Each analysis included 20000 events.

EXAMPLE 14

Histology and Immunohistochemical Analyses

At day 6 (n=10) and day 30 (n=10), hearts were excised. After fixation in 4% phosphate buffered formalin the hearts were cut transversally into 2 mm thick slices and embedded in paraffin. 4 µm thick sections were cut and mounted on positively charged glass slides. Standard histological procedures (hematoxilin/eosin and Masson trichrome) and immunostaining (see below) were performed.

Infarct size was determined as area of infarction (AI) correlated to the area of the left ventricle (including LV-septum) in four different slices from the base to the apex of a heart. Total infarct size was calculated by multiplication of the mean percentage value of the circular infarct area with the quotient: vertical extension of the infarct area/total ventricular extension. Wall thickness was measured by taking the average length of five segments along radii from the centre of the left ventricle through the thinnest points of the free LV wall and the septal wall. All studies were performed by a blinded pathologist.

For immunostaining mounted tissue sections were deparaffinized by rinsing 3×5 minutes in xylene followed by 2×5 minutes 100%, 2×5 minutes 96%, and 2×5 minutes 70% ethanol rinses. Endogenous peroxidases were quenched in 7.5% $H_2O_2$ in distilled water for 10 minutes. After rinsing in distilled water for 10 minutes and 2×5 minutes in TRIS-Buffer, pH 7.5, the slides were incubated at room temperature for 60 minutes with following primary antibodies: CD45 (rat anti-mouse, BD Pharmingen), ICAM-1 (goat anti-mouse, R&D), CD34 (rat anti-mouse, Linaris), Ki67 (goat anti-mouse, Santa Cruz) or BrdU (mouse monoclonal anti-BrdU, BD Pharmingen). Pre-treatment was performed for 30 minutes (microwave 750 W) using TRS 6 (Dako) for CD45, Glykol (biologo) for CD34, Retrievagen A (BD Pharmingen) for BrdU, and citrate buffer (10 mM, pH 6.0) for Ki67.

For detection of the immunoreaction Avidin-Biotinylated enzyme Comlex-Rat IgG, Avidin-Biotinylated enzyme Comlex-Goat IgG (both from Vector) or rabbit anti-goat IgG (DAKO) were used. Aminoethylcarbazol was used as chromogen (incubation 10 minutes). Thereafter, the slides were rinsed in running water and counterstained with hematoxilin Gill's Formula (Vector). Cover slides were mounted with Kaiser's glycerol gelatine. Doublestaining was performed for CD31 and Ki67 using an Avidin-Biotinylated enzyme Comlex-Goat IgG detection system and diaminobenzidine as chromogen and the APAAP-Rat system and chromogen red (all from Dako), respectively.

Quantitative assessments: a) granulation tissue: the number of BrdU and Ki76 positive nuclei were related to the total number of nuclei quantified in the granulation tissue. b) arterioles: only arterioles with high proliferative activity were enclosed.

EXAMPLE 15

Functional Parameters

For evaluation of pressure-volume relationships in vivo, surviving mice of the group 1) MI day 6 (n=6) and day 30 (n=6), 2) MI+PTH day 6 (n=6) and day 30 (n=6), and 3) sham (n=5) and control (n=6) animals were anesthetized with thiopental (100 mg/kg, i.p.), intubated and ventilated (MiniVent, HUGO SACHS, Freiburg, Germany). After catheterization via the right carotid artery an impedance-micromanometer catheter (Millar Instruments, Houston, Tex.) was introduced into the left ventricle. Raw conductance volumes were corrected for parallel conductance by the hypertonic saline dilution method. For absolute volume measurements, the catheter was calibrated with known volumes of heparin treated mouse blood. Pressure-volume signals were recorded at steady state and during transient preload reduction achieved by vena cava occlusion to obtain values independent of cardiac afterload 45. Data analyses were performed as previously described 44 using PVAN analysis software (HUGO SACHS, March, Germany).

EXAMPLE 16

Statistical Analyses

Results were expressed as mean±S.E.M. For statistical analyses the unpaired Student's t-test was used. Mortality was analyzed by the Kaplan-Meier-method. Animals dying within the first 24 hours after surgery or animals having myocardial infarctions smaller than 10% of the LV were not included in the statistical analyses to exclude the influence of perioperative traumas. Data were considered statistically significant at a value of $p \leq 0.05$.

EXAMPLE 17

Mobilization of Bone Marrow Derived Cells by PTH (1-34) Treatment

Peripheral blood samples were analyzed for the number of CD45 positive stem cells. We found a significant increase in CD34, CD31, Sca-1 and c-kit positive stem cell fractions 6 days and to a larger amount 14 days after treatment with PTH (1-34): $CD45^+/CD34^+$, 4.4-fold at day 6 and 6.0 fold at day 14; $CD45^+/CD34^{+/CD}31^+$, 2.9-fold at day 6 and 3.1 fold at day 14; $CD45^+/CD34^+/Sca-1^+$, 2.9-fold at day 6 and 2.9 fold at day 14; $CD45^+/CD34^{+/c-kit+}$, 6.1-fold at day 6 and 9.0 fold at day 14 (Table 1).

TABLE 1

Histological Analysis

| Parameter | Sham | MI + saline, d6 | PTH(1-34) + MI, d6 | MI + saline, d30 | PTH(1-34) + MI, d30 |
|---|---|---|---|---|---|
| Thickness anterior LV wall (mm) | 0.95 ± 0.01 | 0.47 ± 0.06 | 0.61 ± 0.03* | 0.13 ± 0.01† | 0.28 ± 0.05*† |
| Thickness septal wall (mm) | 1.4 ± 0.17 | 1.06 ± 0.09 | 1.05 ± 0.15 | 0.86 ± 0.06 | 1.00 ± 0.06 |
| Infarct size (% LV) | — | 39.8 ± 3.10 | 37.3 ± 4.90 | 33.6 ± 2.60† | 23.3 ± 4.6*† |
| Granulation tissue (% Infarct) | — | 84.4 ± 3.30 | | — | — |

Histological analysis of infarct size (n = 10), LV anterior and septal wall thickness (n = 10) as well as percentage of granulation tissue within the area of infarction (n = 6) at 6 days and 30 days after MI.
MI + saline d6 vs. MI + PTH(1-34) d6 and MI + saline d30 vs. MI + PTH(1-34) d30, *p < 0.05.
MI + saline d6 vs. MI + saline d30 and MI + G-CSF d6 vs. MI + G-CSF d30, †p < 0.05.
Values are mean ± S.E.M.

EXAMPLE 18

Survival 4 Weeks after MI 4 weeks after myocardial infarction, rPTH (1-34) treated mice showed a significant increase in the survival rate compared to saline treated animals (60.0% vs. 40.2%). Mortality amongst untreated animals was very high within the first six days after myocardial infarction, whereas mice surviving the first 6 days after MI showed a lower mortality in both groups (FIG. 4).

EXAMPLE 19

Pressure Volume Relations Measured in a Long Term Follow Up In Vivo

Using conductance catheters pressure volume relations were measured from baseline (sham and control animals), PTH (1-34) treated as well as saline treated mice at day 6 and day 30 after the surgically induced myocardial infarction in vivo (Table 1, FIGS. 5, 6). Compared to baseline, PTH treatment of sham operated animals resulted in a significant reduction in the maximum LV pressure (90.1±3.7 vs. 80.3±2.1 mmHg) whereas the other haemodynamical parameters were in the same range. Saline treated mice as well as PTH treated animals bearing myocardial infarction showed a significantly decreased systolic and diastolic function at day 6 and day 30. However, at day 6 PTH treatment resulted in an improved systolic function reflected by an increased ejection fraction (30 vs. 15%, FIG. 7), cardiac output (5537 vs. 3588 μl/min, FIG. 8) and contractility (4742±394 vs. 3392±358 mmHg/sec). Moreover, arterial vascular load was significantly reduced in PTH treated animals reflected by a decreased arterial elastance ($E_a$: 6.1±0.5 vs. 8.9±0.9 mmHg/μl, FIG. 10). Diastolic function was similar in both groups without significant changes in Tau glantz.

At day 30, hemodynamical improvement was still present in the PTH treated group: Ejection fraction (EF: 29.0±7.1% vs. 14.5±0.9%, p<0.001, FIG. 7), cardiac output (3810±205 vs. 2690±329, FIG. 8) and stroke work (382±59 vs. 258±27 mmHg×μl, p<0.05, FIG. 9) were significantly improved. Similar to the 6 days group arterial elastance ($E_a$: 7.2±0.5 vs. 11.5±1.6 mmHg/μl, FIG. 10) was significantly reduced 30 days after hormone treatment. Moreover, diastolic relaxation tends to be improved after PTH treatment reflected by an accelerated diastolic relaxation (Tau Glantz: 12.0 vs. 14.81±1.5 ms). Furthermore, enddiastolic volumes (EDV: 34.4±6.1 vs. 41.3±3.2) were no significantly reduced in PTH (1-34) treated animals (Table 2).

TABLE 2

Hemodynamical data

| Parameter | baseline (n = 10) | Sham + PTH, d30 (n = 10) | MI + saline, d6 (n = 6) | PTH + MI, d6 (n = 6) | MI + saline, d30 (n = 6) | PTH + MI, d30 (n = 6) |
|---|---|---|---|---|---|---|
| HR (bpm) | 460 ± 4.6 | 434 ± 17 | 434 ± 12 | 479 ± 35 | 427 ± 8 | 422 ± 13 |
| Pmax (mmHg) | 90.1 ± 3.7 | 80.3 ± 2.1† | 62.6 ± 4.0 | 71.5 ± 3.0 | 67.3 ± 4.3 | 65.0 ± 4.2 |
| EDV (μl) | 23.7 ± 2.6 | 27.8 ± 2.9 | 56.4 ± 7.3 | 43.9 ± 7.4 | 41.3 ± 3.2 | 34.4 ± 6.4 |
| Contractile parameters | | | | | | |
| EF (%) | 61.7 ± 2.8 | 59.6 ± 2.5 | 14.5 ± 1.3 | 30.5 ± 6.0† | 14.5 ± 0.9 | 29.5 ± 7.0† |
| CO (μl/min) | 7919 ± 1018 | 7319 ± 563 | 3588 ± 579 | 5537 ± 477† | 2690 ± 329 | 3810 ± 205†* |
| dP/dt max (mmHg/sec) | 5928 ± 427 | 5306 ± 198 | 3392 ± 358 | 4742 ± 394† | 3053 ± 220 | 3468 ± 287* |
| SW (mmHg × μl) | 976 ± 139 | 1091 ± 56 | 349.7 ± 60 | 569 ± 62† | 258 ± 27 | 382 ± 60†* |
| Relaxation parameters | | | | | | |
| Tau Glantz (msec) | 9.8 ± 0.5 | 9.5 ± 0.4 | 11.9 ± 0.6 | 10.3 ± 0.5 | 14.1 ± 1.5 | 12.0 ± 0.08 |
| dP/dt min (mmHg/sec) | -8095 ± 371 | -5884 ± 244 | -3577 ± 351 | -4838 ± 372† | -3112 ± 276 | -3871 ± 468† |
| Arterial Elastance EA (mmHg/μl) | 6.1 ± 0.7 | 5.5 ± 0.4 | 8.9 ± 0.9 | 6.0 ± 0.5† | 11.5 ± 1.6 | 7.1 ± 0.6† |

Pressure volume relations were gained from control and sham operated mice (baseline), from PTH(1-34) treated as well as saline treated mice at day 6 and day 30 after MI in vivo using Millar-tip conductance catheters.
HR: Heart rate, Pmax: maximal pressure of LV, EDV: Enddiastolic volume, EF: Ejection fraction, CO: Cardiac output (HR × stroke volume), SW: Stroke work (Area enclosed by pressure volume loops P × V), Tau-Glantz: regression function of dp/dt vs. pressure, Arterial Elastance: Endsystolic pressure/stroke volume).
MI + saline d6 vs. MI + saline d30 and MI + G-CSF d6 vs. MI + G-CSF d30, *p < 0.05.
MI + saline d6 vs. MI + PTH(1-34) d6 and MI + saline d30 vs. MI + PTH(1-34) d30, †p < 0.05.
Values are mean ± S.E.M.

EXAMPLE 20

Histopathological Changes after PTH (1-34) Treatment

At day 30, saline treated infarcted mice revealed a transmural myocardial infarction with pronounced wall thinning over time and apical aneurysms in, whereas rPTH (1-34) treatment was associated with a lower frequency of large LV-aneurysms (FIG. 6). LV-infarct size at day 6 calculated as area of necrosis and granulation tissue (37.3±4.9% vs. 39.8±3.1% of total LV area, p=ns, FIG. 11) was not significantly different compared to saline treatment. However, infarct composition was altered with a significantly lower cellular density (4383±409 vs. 3317±171/mm$^2$, p<0.05, FIG. 12) in the granulation tissue. At day 30 after LAD occlusion infarct size measured as area of fibrosis was significantly smaller in PTH treated animals (23.3±4.6% vs. 33.6±2.6%, p<0.05, FIG. 11). The anterior wall thickness declined over time in both groups, however, to a smaller extent in G-CSF treated mice (Table 1 & FIG. 6). At day 6 and at day 30 the anterior wall in the group of rPTH treaded animals was thicker compared to saline treated mice (day 6: 0.58 vs. 0.42 mm, day 30: 0.22 vs. 0.13 mm, FIG. 13).

EXAMPLE 21

Cellular Changes after PTH Treatment 6 days after myocardial infarction the granulation tissue of PTH (1-34) treated as well as saline treated animals revealed a strong infiltration of CD45 positive cells, mostly monocytes and granulocytes. To evaluate the amount of cell proliferation we measured BrdU and Ki67 positive cells in the granulation tissue. The number of Ki67 and BrdU positive cells, was not significantly different between PTH and saline treated animals, either within the granulation tissue (Ki67: 34.8±4.8% vs. 52.5±10.4%, p=ns; BrdU: 72.1±2.4% vs. 64.8±6.8%, p=ns) or within the remote area (less than 1%). However, at day 30 we found a significantly higher amount of BrdU positive cells in the periinfarct region (99.1±25.0 vs. 35.6±12.5/mm$^2$). Many of these cells were located between cardiomyocytes. Furthermore, we found high numbers of Ki67 positive endothelial cells that were associated with CD31 positive arterioles in PTH (1-34) treated animals compared to saline treated animals. These vessels were characterized by a layer of smooth muscle cells and were located in the border zone and in the area of granulation tissue of the infarct.

Further investigations on Ki67 positive arterioles revealed an increased expression of ICAM-1, which was associated with a pronounced infiltration of CD45 positive cells. CD34 staining was observed on endothelial cells of capillaries and veins and the adventitia of arteries and further stromal cells, but not on endothelial cells of arterioles or infiltrating cells. Furthermore, there was no obvious difference either in strength of staining or in cell types staining positive for CD34 between G-CSF treated and saline treated mice (data not shown).

EXAMPLE 22

Improvement of Cardiac Function after Myocardial Infarction by Increasing Homing-Capacity Via DPP-IV-Inhibition It was demonstrated that transplantation or mobilisation of stem cells from bone marrow results in improved cardiac function and survival after myocardial infarction in animals. Probably, these effects are rather due to the paracrine potential of stem cells than to real transdifferentiation. However, results of clinical studies of stem cell therapy are ambivalent: Some showed improvement of cardiac function and others were negative. Keeping in mind the striking results of the animal studies, the promising approach of stem cell therapy after myocardial infarction obviously needs modifications and alternatives for clinical use. We believe that one important issue that definitively needs to be addressed is the complex of stem cell homing. This process mainly works through the interaction of myocardial SDF-1 with its receptor CXCR-4 that is expressed on stem cells. An upregulation of myocardial SDF-1 would improve stem cell homing considerably. Therefore, innovative strategies have to concentrate on increasing SDF-1 expression in the myocardium—as intended in the present application:

We have analyzed the effect of administration of the DPP-IV-inhibitor diprotin A after myocardial infarction in a mouse model. Dipeptidyl peptidase IV (DPP-IV or CD26) degrades SDF-1 and can be inhibited by diprotin A. DPP-IV inhibitors like Vildagliptin or Sitagliptin are already approved for clinical use in diabetes mellitus.

In our own studies we could demonstrate that left ventricular ejection fraction is reduced 6 days after acute myocardial infarction ("AMI") in comparison to a control group ("sham", each n=6; 24±5% vs. 67±7%, p<0.05). Myocardial infarction was induced in mice by an established model of LAD-ligation and cardiac function was assessed by catheter-based Millar-tip analysis. In a third group ("AMI+diprA") diprotin A (5 µmol i.p.) was applied twice a day for 5 days after myocardial infarction. In this group, ejection fraction was significantly higher in comparison to the "AMI"-group without DPP-IV-inhibition (49±6 vs. 24±5%, p<0.05).

Our data show (see FIG. 14) that DPP-IV-inhibition via Diprotin A leads to a significantly improved cardiac function after myocardial infarction in a mouse model. DPP-IV inhibitors like Vildagliptin or Sitagliptin are already approved for clinical use in diabetes mellitus.

---

The invention claimed is:

1. A method of repairing and/or regenerating ischemic tissue in a patient in need thereof comprising administering a pharmaceutical composition comprising a peptide comprising amino acids 1-34 of parathyroid hormone (PTH) to a patient in need thereof in an amount which is effective to recruit stem cells into ischemic tissue and repair and/or regenerate said tissue, wherein said pharmaceutical composition is administered at least once daily for at least one day.

2. The method of claim 1, wherein said stem cells are selected from the group consisting of:
   a) CD34(+)/CD45(+) and CD34(−)/CD45(+) cells, each in combination with the subpopulations CD31 (+), Sca-1 (+) or C-kit(+),
   b) multipotent adult progenitor cells (MAPC),
   c) endothelial progenitor cells (EPC) characterized by CD34(+), CD45(+), CD31(+),
   d) side population cells (SP) and
   e) lineage-negative stem cells, lin(−), c-kit(+).

3. The method of claim 1, wherein said pharmaceutical composition is administered subcutaneously.

4. The method of claim 1, wherein said ischemia is selected from the group consisting of myocardial ischemia, cerebral ischemia, renal ischemia, liver ischemia, peripheral muscle tissue ischemia, retinal ischemia and spinal cord ischemia.

5. The method of claim 3, wherein said myocardial ischemia is caused by heart failure, hypertension, coronary artery disease (CAD), myocardial infarction, thrombo-embolic events, trauma, surgical and/or interventional measures.

6. The method of claim 5, wherein said surgical or interventional measure is a procedure to regain blood flow selected from the group consisting of thrombolysis, balloon angioplasty, stenting, coronary or peripheral bypass surgery and ventriculo-coronary stenting.

7. The method of claim 1, wherein said pharmaceutical composition further comprises human G-CSF.

8. The method of claim 1, wherein said pharmaceutical composition further comprises a DPP IV antagonist selected from the group consisting of Diprotin A, Vildagliptin and Sitagliptin.

9. The method of claim 1, wherein said ischemia is myocardial ischemia caused by myocardial infarction.

10. A method of repairing and/or regenerating ischemic tissue in a patient in need thereof comprising subcutaneously administering a pharmaceutical composition comprising a peptide comprising amino acids 1-34 of parathyroid hormone (PTH) to a patient in need thereof in an amount which is effective to recruit stem cells into ischemic tissue and repair and/or regenerate said tissue.

11. A method of repairing and/or regenerating ischemic tissue in a patient in need thereof comprising administering a pharmaceutical composition comprising (A) a DPP IV antagonist selected from the group consisting of Diprotin A, Vildagliptin and Sitagliptin and (B) a peptide comprising amino acids 1-34 of parathyroid hormone (PTH) to a patient in need thereof in an amount which is effective to recruit stem cells into ischemic tissue and repair and/or regenerate said tissue.

12. A method of repairing and/or regenerating ischemic tissue in a patient in need thereof comprising administering a pharmaceutical composition comprising a peptide comprising amino acids 1-34 of parathyroid hormone (PTH) to a patient in need thereof in an amount which is effective to recruit stem cells into ischemic tissue and repair and/or regenerate said tissue, wherein said ischemia is myocardial ischemia caused by a surgical and/or interventional measure which is a procedure to regain blood flow selected from the group consisting of thrombolysis, balloon angioplasty, stenting, coronary or peripheral bypass surgery and ventriculo-coronary stenting.

* * * * *